US008614344B2

(12) United States Patent
Kaido et al.

(10) Patent No.: US 8,614,344 B2
(45) Date of Patent: Dec. 24, 2013

(54) METATHESIS METHODS INVOLVING HYDROGENATION AND COMPOSITIONS RELATING TO SAME

(75) Inventors: Hiroki Kaido, Eden Prairie, MN (US); Michael John Tupy, Crystal, MN (US); Richard L. Pederson, San Gabriel, CA (US); Yann Schrodi, Agoura Hills, CA (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 410 days.

(21) Appl. No.: 12/444,791

(22) PCT Filed: Oct. 15, 2007

(86) PCT No.: PCT/US2007/021934

§ 371 (c)(1), (2), (4) Date: Dec. 3, 2009

(87) PCT Pub. No.: WO2008/063322

PCT Pub. Date: May 29, 2008

(65) Prior Publication Data

US 2010/0094034 A1 Apr. 15, 2010

Related U.S. Application Data

(60) Provisional application No. 60/851,628, filed on Oct. 13, 2006.

(51) Int. Cl.
*C07C 51/36* (2006.01)

(52) U.S. Cl.
USPC .......... 554/145

(58) Field of Classification Search
USPC .......... 554/145
See application file for complete search history.

(56) References Cited

U.S. PATENT DOCUMENTS

| | | | |
|---|---|---|---|
| 3,896,053 | A | 7/1975 | Broecker et al. |
| 5,043,485 | A | 8/1991 | Fleckenstein et al. |
| 5,142,072 | A | 8/1992 | Stipp et al. |

(Continued)

FOREIGN PATENT DOCUMENTS

| | | | |
|---|---|---|---|
| EP | 0429995 | A2 | 6/1991 |
| EP | 1408064 | A1 | 4/2004 |

(Continued)

OTHER PUBLICATIONS

International Search Report and Written Opinion of the International Searching Authority for International Application No. PCT/US2007/021934, dated Jun. 17, 2008, 7 pages.

(Continued)

*Primary Examiner* — Deborah D Carr
(74) *Attorney, Agent, or Firm* — Brinks Hofer Gilson & Lione

(57) ABSTRACT

Disclosed are improved methods for conducting metathesis utilizing polyunsaturated fatty acid compositions (e.g., polyunsaturated fatty acid polyol esters, polyunsaturated fatty acids, polyunsaturated fatty esters, and mixtures), such as those found in naturally occurring oils and fats, as the starting material. The inventive methods involve hydrogenation of polyunsaturated fatty acid compositions prior to metathesis, thereby providing partially-hydrogenation compositions having a relatively higher amount of monounsaturated fatty acid species. The partially hydrogenated composition can then be subjected to metathesis to provide a metathesis product composition containing industrially useful compounds.

22 Claims, 2 Drawing Sheets

(56) References Cited

U.S. PATENT DOCUMENTS

| | | | | |
|---|---|---|---|---|
| 5,734,070 | A | 3/1998 | Tacke et al. | |
| 6,197,894 | B1 | 3/2001 | Sunaga et al. | |
| 6,211,315 | B1 | 4/2001 | Larock et al. | |
| 6,281,163 | B1 | 8/2001 | Van Dijk | |
| 6,486,264 | B1 | 11/2002 | Tsunogae et al. | |
| 6,696,597 | B2 | 2/2004 | Pederson et al. | |
| 6,716,155 | B2 | 4/2004 | Sleeter | |
| 6,900,347 | B2 | 5/2005 | Paulson et al. | |
| 6,962,729 | B2 | 11/2005 | Tokas et al. | |
| 6,987,154 | B2 | 1/2006 | Choi et al. | |
| 7,026,495 | B1 | 4/2006 | Pederson et al. | |
| 7,119,216 | B2 | 10/2006 | Newman et al. | |
| 7,176,336 | B2 | 2/2007 | Maughon et al. | |
| 7,314,904 | B2 | 1/2008 | Nadolsky et al. | |
| 7,365,140 | B2 | 4/2008 | Piers et al. | |
| 7,576,227 | B2 | 8/2009 | Lysenko et al. | |
| 7,585,990 | B2 | 9/2009 | van Toor et al. | |
| 7,678,932 | B2 | 3/2010 | Thurier et al. | |
| 7,812,185 | B2 | 10/2010 | Burdett et al. | |
| 2002/0095007 | A1 | 7/2002 | Larock et al. | |
| 2005/0027136 | A1 | 2/2005 | Toor et al. | |
| 2006/0079704 | A1 | 4/2006 | Lacombe et al. | |
| 2006/0289138 | A1 | 12/2006 | Borsinger et al. | |
| 2007/0179307 | A1 | 8/2007 | Olivier-Bourbigou et al. | |
| 2007/0270621 | A1 | 11/2007 | Millis et al. | |
| 2008/0027194 | A1 | 1/2008 | Schrodi | |
| 2008/0064891 | A1 | 3/2008 | Lee | |
| 2009/0048459 | A1 | 2/2009 | Tupy et al. | |
| 2009/0126602 | A1 * | 5/2009 | Murphy et al. | 106/251 |
| 2009/0217568 | A1 | 9/2009 | Murphy et al. | |
| 2009/0220443 | A1 | 9/2009 | Braksmayer et al. | |
| 2009/0259065 | A1 | 10/2009 | Abraham et al. | |
| 2009/0264672 | A1 | 10/2009 | Abraham et al. | |
| 2010/0047499 | A1 | 2/2010 | Braksmayer et al. | |
| 2010/0145086 | A1 | 6/2010 | Schrodi et al. | |

FOREIGN PATENT DOCUMENTS

| | | | |
|---|---|---|---|
| EP | 1810960 | A1 | 7/2007 |
| FR | 2878246 | A1 | 5/2006 |
| JP | 56-077243 | A | 6/1981 |
| JP | 09-014574 | A | 1/1997 |
| SU | 1565872 | A1 | 7/1988 |
| WO | WO 94/23836 | A1 | 10/1994 |
| WO | WO 96/04289 | A1 | 2/1996 |
| WO | WO 01/36368 | A2 | 5/2001 |
| WO | WO 03/093215 | A1 | 11/2003 |
| WO | WO 2004/062763 | A2 | 7/2004 |
| WO | WO 2005/080455 | A1 | 9/2005 |
| WO | WO 2006/052688 | A2 | 5/2006 |
| WO | WO 2007/081987 | A2 | 7/2007 |
| WO | WO 2007/103398 | A1 | 9/2007 |
| WO | WO 2007/103460 | A2 | 9/2007 |
| WO | WO 2008/008420 | A1 | 1/2008 |
| WO | WO 2008/010961 | A2 | 1/2008 |
| WO | WO 2008/048520 | A2 | 4/2008 |
| WO | WO 2008/063322 | A2 | 5/2008 |
| WO | WO 2008/140468 | A2 | 11/2008 |

OTHER PUBLICATIONS

Anderson et al., "Synthesis and Reactivity of Olefin Metathesis Catalysts Bearing Cyclic (Alkyl)(Amino) Carbenes," Angewandte Chemie International Edition, vol. 46, 2007, pp. 7262-7265.

Baumann et al., "Natural Fats and Oils—Renewable Raw Materials for the Chemical Industry," Angewandte Chemie International Edition in English, vol. 27, 1988, pp. 41-62.

Biermann et al., "New Syntheses with Oils and Fats as Renewable Raw Materials for the Chemical Industry,", Angewandte Chemie International Edition, vol. 39, 2000, pp. 2206-2224.

Boelhouwer et al., "Metathesis Reactions of Fatty Acid Esters," Progress of Lipid Research, Pergamon Press, vol. 24, No. 3, 1985, pp. 243-267.

Choi et al., "Olefin Metathesis Involving Ruthenium Enoic Carbene Complexes," Journal of the American Chemical Society, vol. 123, No. 42, 2001, pp. 10417-10418.

Connon et al., "A Solid-Supported Phosphine-Free Ruthenium Alkylidene for Olefin Metathesis in Methanol and Water," Bioorganic & Medical Chem Letters, vol. 12, No. 14, 2002, pp. 1873-1876.

Dunne et al., "A Highly Efficient Olefin Metathesis Initiator: Improved Synthesis and Reactivity Studies," Tetrahedron Letters, vol. 44, No. 13, 2003, pp. 2733-2736.

Erhan et al. , "Drying Properties of Metathesized Soybean Oil," Journal of American Oil Chemists' Society, AOCS Press, vol. 74, No. 6, 1997, pp. 703-706.

Lavallo, "Stable Cyclic (Alkyl)(Amino) Carbenes as Rigid or Flexible, Bulky, Electron-Rich Ligands for Transition-Metal Catalysts: A Quaternary Carbon Atom Makes the Difference," Angewandte Chemie Int. Ed., vol. 44, 2005, pp. 5705-5709.

Maynard et al., "Purification Technique for the Removal of Ruthenium from Olefin Metathesis Reaction Products," Tetrahedron Letters, vol. 40, No. 22, 1999, pp. 4137-4140.

Mol, "Applications of Olefin Metathesis in Oleochemistry: An Example of Green Chemistry," Green Chemistry, Royal Society of Chemistry, Cambridge, GB, vol. 4, 2002, pp. 5-13.

Mol et al., "Metathesis in Oleochemistry," J Braz Chem Soc, vol. 9, No. 1, 1998, pp. 1-11.

Mol, "Catalytic Metathesis of Unsaturated Fatty Acid Esters and Oils," Topics in Catalysis, vol. 27, No. 1-4, 2004, pp. 97-104.

Patel et al., "High conversion and productive catalyst turnovers in cross-metathesis reactions of natural oils with 2-butene", Green Chemistry, 2006, vol. 8, pp. 450-454.

Refvik et al., "Ruthenium-Catalyzed Metathesis of Vegetable Oils," Journal of American Oil Chemists' Society, AOCS Press, vol. 76, No. 1, 1999, pp. 93-98.

Schneider et al., "Synthesis of Highly Substituted Cyclopentane and Tetrahydrofuran Derivatives by Crossed Olefin Metathesis," Angewandte Chemi International Edition, vol. 35, No. 4, 1996, pp. 411-412.

Tian et al., "Model Studies and the ADMET Polymerization of Soybean Oil," Journal of American Oil Chemists' Society, AOCS Press, vol. 79, No. 5, 2002, pp. 479-488.

Refvik, M.D. et al., "The Chemistry of Metathesized Soybean Oil," JAOCS, vol. 76, No. 1, 1999, pp. 99-102.

Chatterjee et al., "Synthesis of Trisubstituted Alkenes via Olefin Cross-Metathesis," Organic Letters, vol. 1, No. 11, 1999, pp. 1751-1753.

Delaude et al., Metathesis, Kirk-Othmer Encyclopedia of Chemical Technology, Dec. 2005, vol. 26, pp. 920-958.

Ngo et al., Methathesis of Unsaturated Fatty Acids: Synthesis of Long-Chain Unsaturated-[alpha],[omega]-Dicarboxylic Acids, Journal of the American Oil Chemists, Jul. 2006, vol. 83m Issue 7, p. 629, 9 pgs.

* cited by examiner

FIG. 3 Kinetic plots of product composition at 80 psi and 0.6% Cu

METATHESIS METHODS INVOLVING HYDROGENATION AND COMPOSITIONS RELATING TO SAME

CROSS-REFERENCE TO RELATED APPLICATIONS

This application claims the benefit under 35 U.S.C. §371 of International Application No. PCT/US2007/021934, filed Oct. 15, 2007, which claims the benefit of U.S. Provisional Application Ser. No. 60/851,628, filed Oct. 13, 2006, and entitled METATHESIS METHODS INVOLVING HYDROGENATION AND COMPOSITIONS RELATING TO SAME, the disclosures of which are incorporated herein by reference.

GOVERNMENT RIGHTS

This invention was made with U.S. Government support under Award Number DE-FG36-04GO14016. The Government may have certain rights in this invention.

BACKGROUND

Metathesis is a catalytic reaction and involves the interchange of alkylidene units among olefinic hydrocarbons via the formation and cleavage of carbon-carbon double bonds. The metathesis reaction may occur between two of the same type of molecules, referred to as self-metathesis, and/or may occur between two dissimilar types of molecules, referred to as cross-metathesis. Metathesis is a well-known and useful synthetic step in the production of industrial chemicals. Metathesis reactions are typically catalyzed by transition metal carbene complexes, for example, complexes comprising ruthenium, molybdenum, osmium, chromium, rhenium, or tungsten.

When metathesis is performed with polyunsaturated hydrocarbons as starting material, added costs and complexity are introduced into the reaction. Each carbon-carbon double bond in the system is a potential reaction site for the metathesis catalyst and also a potential site for catalyst deactivation. Unneeded sites of reaction increase the catalyst demand and can increase the complexity of the reaction product mixture. This is especially apparent in the self-metathesis of polyunsaturated fatty acid esters, where the metathesis product is a complex mixture of multiple diesters, monoesters, and internal olefins.

A specific complication arises in the self-metathesis of naturally occurring oils comprising polyunsaturated species (e.g., polyunsaturated polyol esters, polyunsaturated fatty acids, or polyunsaturated free fatty esters). The naturally occurring methylene interrupted cis, cis configuration that is prevalent in most of these oils can form 6-carbon structures, for example, cyclohexadienes having the carbon-carbon double bonds at various locations in the ring. These molecules represent volatile organic components (VOC) as part of the product, which leads to a loss in yield and a potential safety hazard. Therefore, it would be beneficial to selectively reduce the number of double bonds in the polyunsaturated compositions to compositions containing monounsaturated species in order to achieve better catalyst efficiency, reduce VOC production, and attenuate product losses.

SUMMARY

The invention provides improved methods for conducting metathesis utilizing polyunsaturated fatty acid compositions (e.g., polyunsaturated fatty acids, polyunsaturated fatty esters (including polyunsaturated monoesters and polyol esters having at least one polyunsaturated fatty acid), such as those found in naturally occurring oils and fats, as the starting material. The inventive methods involve hydrogenation of polyunsaturated fatty acid compositions prior to metathesis, thereby providing partially-hydrogenated compositions having a relatively higher amount of monounsaturated fatty acid species (e.g., monounsaturated fatty acids, monounsaturated fatty esters, or polyol esters comprising one or more monounsaturated fatty acids) than the starting polyunsaturated fatty acid composition. The partially hydrogenated composition can then be subjected to metathesis to provide a metathesis product composition containing industrially useful compounds. For example, when the partially hydrogenated product is a free fatty acid or a free fatty ester that is subjected to self-metathesis, the metathesis product composition can comprise a monounsaturated diacid or a monounsaturated diester, respectfully. Additionally, by way of example, when the partially hydrogenated product is a fatty acid or ester that is subjected to cross-metathesis with a terminal olefin, the metathesis product composition can comprise a mixture of linear fatty acids or esters. The linear fatty esters can be hydrolyzed to produce linear fatty acids. Advantageously, the latter method provides an efficient method of preparing linear fatty acids having terminal double bonds.

In some embodiments, the terminal linear fatty acids have a chain length in the range of 3 to n carbon atoms (where n is the chain length of the partially hydrogenated composition which has a double bond at the 2 to (n−1) position after partial hydrogenation). In other embodiments, the terminal fatty acids have a chain length in the range of 5 to (n−1) carbon atoms (where n is the chain length of the partially hydrogenated composition, which has a double bond at the 4 to (n−2) position after partial hydrogenation). In exemplary embodiments, the terminal fatty acids have a chain length in the range of 5 to 17 carbon atoms.

In some embodiments, the monounsaturated diesters or diacids have a chain length in the range of 4 to (2n−2) carbon atoms (where n is the chain length of the partially hydrogenated composition which has a double bond at the 2 to (n−1) position after partial hydrogenation). In other embodiments, the monounsaturated diesters or diacids have a chain length in the range of 8 to (2n−4) carbon atoms (where n is the chain length of the partially hydrogenated composition, which has a double bond at the 4 to (n−2) position after partial hydrogenation). In exemplary embodiments, the monounsaturated diesters of diacids have a chain length in the range of 8 to 32 carbon atoms. According to the invention, the starting material comprises a polyunsaturated fatty acid composition that can be derived, for example, from a naturally-occurring fat or oil. In some embodiments, the oil is a vegetable oil, such as soybean oil. Main unsaturated fatty acids in vegetable oils are linolenic acid (cis-9, cis-12, cis-15 octadecatrienoic acid, C18:3), linoleic acid (cis-9, cis-12 octadecadienoic acid, C18:2) and oleic acid (cis-9-octadecenoic acid, C18:1). The existence of polyunsaturation within the fatty acids of natural oils can be a source of reaction inefficiency (e.g., by increasing metathesis catalyst demand, by increasing reaction byproducts, and the like) in metathesis. The inventive methods can utilize renewable resources for generation of industrially useful compounds. In preferred aspects, the inventive methods can provide more efficient reaction conditions for metathesis.

In some aspects, the invention provides a method comprising steps of: (a) providing a polyunsaturated fatty acid composition; (b) providing a hydrogenation catalyst; (c) hydrogenating at least a portion of the polyunsaturated fatty acid composition in the presence of the hydrogenation catalyst to form a partially hydrogenated composition; (d) providing a metathesis catalyst comprising a transition metal; and (e) metathesizing at least a portion of the partially hydrogenated composition in the presence of the metathesis catalyst to form a composition comprising a mixture of metathesis products.

The inventive methods, which combine a hydrogenation reaction prior to a metathesis reaction can provide one or more benefits. For example, hydrogenation prior to metathesis can reduce polyunsaturation in the polyunsaturated fatty acid composition, thereby providing a partially hydrogenated composition that is more suitable for metathesis reaction. For example, reduction in the number of carbon-carbon double bonds in the polyunsaturated fatty acid composition can reduce catalyst demand, since each carbon-carbon double bond is a reaction site for catalyst and can result in irreversible deactivation of the catalyst. Moreover, multiple potential reaction sites within the polyunsaturated composition can provide a complex mixture of products. By selectively removing polyunsaturation prior to metathesis, the inventive methods can reduce the amount of byproducts that can be formed during metathesis. In some aspects, hydrogenation prior to metathesis can reduce generation of unwanted byproducts such as cyclohexadiene and other volatile organic compounds (VOCs).

In some aspects, the inventive methods involve hydrogenation prior to cross-metathesis with a small olefin (such as ethylene, propylene, 1-butene, 2-butene, 2-pentene, 2-hexene, 3-hexene, and the like). Generally speaking, during metathesis of polyunsaturates, short chain di-olefins can be generated in the metathesis reaction, such as 1,4-pentadiene, and the like. Such short chain di-olefins can complex with the metathesis catalyst and may deactivate the catalyst. Thus, in some aspects, the inventive methods provide the ability to reduce the amount of polyunsaturates within the metathesis reaction, thereby reducing generation of these short chain di-olefins and improving catalyst efficiency.

In some aspects, the preferred metathesis catalysts are neutral ruthenium or osmium metal carbene complexes that possess metal centers that are formally in the +2 oxidation state, have an electron count of 16, and are penta-coordinated. Other preferred metathesis catalysts include cationic ruthenium or osmium metal carbene complexes that possess metal centers that are formally in the +2 oxidation state, have an electron count of 14, and are tetra-coordinated. Examples of such metathesis catalysts have been previously described in, for example, U.S. Pat. Nos. 6,900,347, 5,312,940; 5,969,170; 5,917,071; 5,977,393; 6,111,121; 6,211,391 and 6,225,488 and PCT Publications WO 98/39346, WO 99/00396, WO 99/00397, WO 99/28330, WO 99/29701, WO 99/50330, WO 99/51344, WO 00/15339, WO 00/58322 and WO 00/71554, the disclosures of each of which are incorporated herein by reference.

These and other aspects and advantages of the inventive concepts will now be described in more detail.

BRIEF DESCRIPTION OF THE DRAWINGS

The accompanying drawings, which are incorporated in and constitute a part of this specification, illustrate several aspects of the invention and together with the description of the various embodiments, serve to explain the principles of the invention. A brief description of the drawings is as follows.

DETAILED DESCRIPTION

Figure 1:
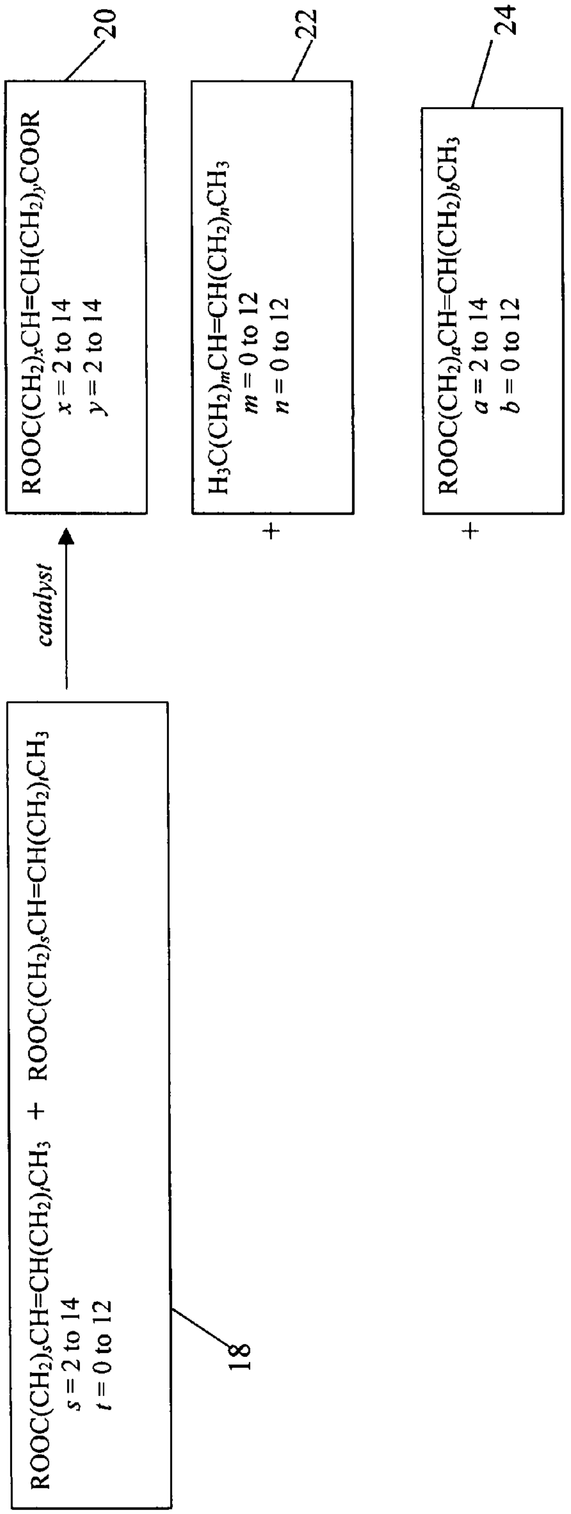
FIG. 1 is an exemplary self-metathesis reaction scheme.

The embodiments of the invention described below are not intended to be exhaustive or to limit the invention to the precise forms disclosed in the following detailed description. Rather, the embodiments are chosen and described so that others skilled in the art can appreciate and understand the principles and practices of the invention.

Throughout the specification and claims, percentages are by weight and temperatures in degrees Celsius unless otherwise indicated.

Starting Materials

As a starting composition, the method of the present invention uses polyunsaturated fatty acid compositions, for example, polyunsaturated fatty acids (or carboxylate salts thereof), polyunsaturated fatty esters (including polyunsaturated monoesters and polyol esters with at least one polyunsaturated fatty acid). Mixtures of the foregoing may also be used. As used herein the term "polyunsaturated fatty acid" refers to compounds that have a polyunsaturated alkene chain with a terminal carboxylic acid group. The alkene chain may be a linear or branched and may optionally include one or more functional groups in addition to the carboxylic acid group. For example, some polyunsaturated fatty acids include one or more hydroxyl groups. The polyunsaturated alkene chain typically contains about 4 to about 30 carbon atoms, more typically about 4 to about 22 carbon atoms. In many embodiments, the alkene chain contains 18 carbon atoms (i.e., a C18 fatty acid). The unsaturated fatty acids have at least two carbon-carbon double bonds in the alkene chain. In exemplary embodiments, the polyunsaturated fatty acid has from 2 to 3 carbon-carbon double bonds in the alkene chain.

Also useful as starting compositions are polyunsaturated fatty esters. As used herein the term "polyunsaturated fatty ester" refers to compounds that have a polyunsaturated alkene chain with a terminal ester group. The alkene chain may be linear or branched and may optionally include one or more functional groups in addition to the ester group. For example, some polyunsaturated fatty esters include one or more hydroxyl groups in addition to the ester group. Polyunsaturated fatty esters include "polyunsaturated monoesters" and "polyunsaturated polyol esters". Polyunsaturated monoesters comprise a polyunsaturated fatty acid that is esterified to a monofunctional alcohol. Polyunsaturated polyol esters have at least one polyunsaturated fatty acid that is esterified to a polyfunctional alcohol (e.g., ethylene glycol, propylene glycol, glycerol, trimethylolpropane, erythritol, sorbitol etc). The alkene chain of polyunsaturated monoesters or polyol esters typically contains about 4 to about 30 carbon atoms, more typically about 4 to 22 carbon atoms. In exemplary embodiments, the alkene chain contains 18 carbon atoms (i.e., a C18 fatty ester). Being polyunsaturated, the alkene chain in polyunsaturated monoesters have at least two carbon-carbon double bonds and may have more than two double bonds. In exemplary embodiments, the unsaturated fatty ester has 2 to 3 carbon-carbon double bonds in the alkene chain. In polyol esters, at least one fatty acid in the polyol ester is a polyunsaturated fatty acid. The remaining fatty acids making up the polyol ester may be saturated, monounsaturated, or polyunsaturated.

Also useful as a starting composition are metal salts of polyunsaturated fatty acids (i.e., carboxylate salts of polyunsaturated fatty acids). The metal salts may be salts of alkali metals (e.g., a group IA metal such as Li, Na, K, Rb, and Cs);

alkaline earth metals (e.g., group IIA metals such as Be, Mg, Ca, Sr, and Ba); group IIIA metals (e.g., B, Al, Ga, In, and Tl); group IVA metals (e.g., Sn and Pb), group VA metals (e.g., Sb and Bi), transition metals (e.g., Sc, Ti, V, Cr, Mn, Fe, Co, Ni, Cu, Zn, Zr, Mo, Ru, Rh, Pd, Ag and Cd), lanthanides or actinides.

In many embodiments, the polyunsaturated fatty acid, ester, or carboxylate salt has a straight alkene chain and can be represented by the general formula:

$$CH_3—(CH_2)_{n1}—[—(CH_2)_{n3}—CH{=}CH—]_x—(CH_2)_{n2}—COOR$$

where:

R is hydrogen (fatty acid), an aliphatic or aromatic group (fatty ester), or a metal ion (carboxylate salt);

n1 is an integer equal to or greater than 0 (typically 0 to 15; more typically 0, 3, or 6);

n2 is an integer equal to or greater than 0 (typically 2 to 11; more typically 3, 4, 7, 9, or 11);

n3 is an integer equal to or greater than 0 (typically 0 to 6; more typically 1); and x is an integer equal to or greater than 2 (typically 2 to 6, more typically 2 to 3).

A summary of some polyunsaturated fatty acids and esters is provided in TABLE A.

Depending upon the make-up of the polyunsaturated triglyceride, the above reaction may yield one, two, or three moles of polyunsaturated monoester. Transesterification is typically conducted in the presence of a catalyst, for example, alkali catalysts, acid catalysts, or enzymes. Representative alkali transesterification catalysts include NaOH, KOH, sodium and potassium alkoxides (e.g., sodium methoxide), sodium ethoxide, sodium propoxide, sodium butoxide. Representative acid catalysts include sulfuric acid, phosphoric acid, hydrochloric acid, and sulfonic acids. Organic or inorganic heterogeneous catalysts may also be used for transesterification. Organic heterogeneous catalysts include sulfonic and fluorosulfonic acid-containing resins. Inorganic heterogeneous catalysts include alkaline earth metals or their salts such as CaO, MgO, calcium acetate, barium acetate, natural clays, zeolites, Sn, Ge or Pb, supported on various materials such as ZnO, MgO, $TiO_2$, activated carbon or graphite, and inorganic oxides such as alumina, silica-alumina, boria, oxides of P, Ti, Zr, Cr, Zn, Mg, Ca, and Fe. In exemplary embodiments, the triglyceride is transesterified with methanol ($CH_3OH$) in order to form free fatty acid methyl esters.

In some embodiments, the polyunsaturated fatty esters are polyunsaturated polyol esters. As used herein the term "polyunsaturated polyol ester" refers to compounds that have at

TABLE A

Unsaturated Fatty Acids/Esters

| Type | General Formula | Examples of fatty acids | Examples of fatty esters |
|---|---|---|---|
| Polyunsaturated | Diunsaturated $CH_3—(CH_2)_{n1}—[—(CH_2)_{n3}—CH{=}CH—]_x—(CH_2)_{n2}—COOR$ Where x is 2, and n1, n2, n3, and R are as described above. | Linoleic acid (x = 2, n1 = 3; n2 = 7; n3 = 1; and R is H.) | Methyl Linoleate (x = 2, n1 = 3; n2 = 7; n3 = 1; and R is CH3.) |
| | Triunsaturated $CH_3—(CH_2)_{n1}—[—(CH_2)_{n3}—CH{=}CH—]_x—(CH_2)_{n2}—COOR$ Where x is 3, and n1, n2, n3, and R are as described above. | Linolenic acid (x = 3, n1 = 0; n2 = 7; n3 = 1; and R is H.) | Methyl Linolenate (x = 3, n1 = 0; n2 = 7; n3 = 1; and R is CH3.) |

Polyunsaturated monoesters may be alkyl esters (e.g., methyl esters) or aryl esters and may be derived from polyunsaturated fatty acids or polyunsaturated glycerides by transesterifying with a monohydric alcohol. The monohydric alcohol may be any monohydric alcohol that is capable of reacting with the unsaturated free fatty acid or unsaturated glyceride to form the corresponding unsaturated monoester. In some embodiments, the monohydric alcohol is a C1 to C20 monohydric alcohol, for example, a C1 to C12 monohydric alcohol, a C1 to C8 monohydric alcohol, or a C1 to C4 monohydric alcohol. The carbon atoms of the monohydric alcohol may be arranged in a straight chain or in a branched chain structure, and may be substituted with one or more substituents. Representative examples of monohydric alcohols include methanol, ethanol, propanol (e.g., isopropanol), and butanol. Transesterification of a polyunsaturated triglyceride can be represented as follows.

1 Polyunsaturated Triglyceride+3 Alcohol→1 Glycerol+1-3 Polyunsaturated Monoester least one polyunsaturated fatty acid that is esterified to the hydroxyl group of a polyol. The other hydroxyl groups of the polyol may be unreacted, may be esterified with a saturated fatty acid, or may be esterified with a monounsaturated fatty acid. Examples of polyols include glycerol and 1,3 propanediol. In many embodiments, unsaturated polyol esters have the general formula:

$$R(O—Y)_m(OH)_n(O—X)_b,$$

where

R is an organic group having a valency of (n+m+b);

m is an integer from 0 to (n+m+b−1), typically 0 to 2;

b is an integer from 1 to (n+m+b), typically 1 to 3;

n is an integer from 0 to (n+m+b−1), typically 0 to 2;

(n+m+b) is an integer that is 2 or greater;

X is $—(O)C—(CH_2)_{n2}—[—CH{=}CH—(CH_2)_{n3}—]_x—(CH_2)_{n1}—CH_3$;

Y is —(O)C—R';

R' is a straight or branched chain alkyl or alkenyl group;

n1 is an integer equal to or greater than 0 (typically 0 to 15; more typically 0, 3, or 6);

n2 is an integer equal to or greater than 0 (typically 2 to 11; more typically 3, 4, 7, 9, or 11);

n3 is an integer equal to or greater than 0 (typically 0 to 6; more typically 1); and x is an integer equal to or greater than 2 (typically 2 to 6, more typically 2 to 3).

In many embodiments, the polyunsaturated polyol esters are polyunsaturated glycerides. As used herein the term "polyunsaturated glyceride" refers to a polyol ester having at least one (e.g., 1 to 3) polyunsaturated fatty acid that is esterified to a molecule of glycerol. The fatty acid groups may be linear or branched and may include pendant hydroxyl groups. In many embodiments, polyunsaturated glycerides are represented by the general formula:

$CH_2A$-$CHB$—$CH_2C$ where

-A; —B; and —C are selected from

—OH;

—O(O)C—$(CH_2)_{n2}$—[—CH═CH—$(CH_2)_{n3}$—$]_x$—$(CH_2)_{n1}$—$CH_3$; and

—O(O)C—R';

with the proviso that at least one of -A, —B, or —C is

—O(O)C—$(CH_2)_{n2}$—[—CH═CH—$(CH_2)_{n3}$—$]_x$—$(CH_2)_{n1}$—$CH_3$.

In the above formula:

R' is a straight or branched chain alkyl or alkenyl group;

n1 is an integer equal to or greater than 0 (typically 0 to 15; more typically 0, 3, or 6);

n2 is an integer equal to or greater than 0 (typically 2 to 11; more typically 3, 4, 7, 9, or 11);

n3 is an integer equal to or greater than 0 (typically 0 to 6; more typically 1); and x is an integer equal to or greater than 2 (typically 2 to 6, more typically 2 to 3).

Polyunsaturated glycerides having two —OH groups (e.g., -A and —B are —OH) are commonly known as unsaturated monoglycerides. Unsaturated glycerides having one —OH group are commonly known as unsaturated diglycerides. Unsaturated glycerides having no —OH groups are commonly known as unsaturated triglycerides.

As shown in the formula above, the polyunsaturated glyceride may include monounsaturated fatty acids, polyunsaturated fatty acids, and saturated fatty acids that are esterified to the glycerol molecule. The main chain of the individual fatty acids may have the same or different chain lengths. Accordingly, the unsaturated glyceride may contain up to three different fatty acids so long as at least one fatty acid is a polyunsaturated fatty acid.

In many embodiments, useful starting compositions are derived from natural oils such as plant-based oils or animal fats. Representative examples of plant-based oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, castor oil, tall oil, and the like. Representative examples of animal fats include lard, tallow, chicken fat (yellow grease), and fish oil. Other useful oils include tall oil and algae oil.

In many embodiments, the plant-based oil is soybean oil. Soybean oil comprises unsaturated glycerides, for example, in many embodiments about 95% weight or greater (e.g., 99% weight or greater) triglycerides. Major fatty acids making up soybean oil include saturated fatty acids, palmitic acid (hexadecanoic acid) and stearic acid (octadecanoic acid), and unsaturated fatty acids, oleic acid (9-octadecenoic acid), linoleic acid (9,12-octadecadienoic acid), and linolenic acid (9,12,15-octadecatrienoic acid). Soybean oil is a highly unsaturated vegetable oil with many of the triglyceride molecules having at least two unsaturated fatty acids.

In many embodiments, the starting composition comprises about 5% weight or greater of polyunsaturated fatty acids, polyunsaturated fatty esters, or carboxylate salts of polyunsaturated fatty acids.

In many embodiments, the starting composition comprises a Δ9 polyunsaturated fatty acid, a Δ9 polyunsaturated fatty ester (e.g., monoesters or polyol esters), a carboxylate salt of a Δ9 polyunsaturated fatty acid, or mixtures of two or more of the foregoing. Δ9 polyunsaturated starting compositions have at least two carbon-carbon double bonds with one of the carbon-carbon double bonds being located between the $9^{th}$ and $10^{th}$ carbon atoms (i.e., between C9 and C10) in the alkene chain of the polyunsaturated fatty acid, ester, or carboxylate salt. In determining this position, the alkene chain is numbered starting with the carbon atom in the carbonyl group of the unsaturated fatty acid, ester, or salt. Included within the definition of Δ9 polyunsaturated fatty acids, esters, and carboxylate salts are Δ9,12 polyunsaturated fatty acids, esters and carboxylate salts, and Δ9,12,15 polyunsaturated fatty acids, esters and carboxylate salts.

In many embodiments, the Δ9 unsaturated starting materials have a straight alkene chain and may be represented by the general structure:

$CH_3$—$(CH_2)_{n1}$—[—$(CH_2)_{n3}$—CH═CH—$]_x$—$(CH_2)_7$—COOR where

R is hydrogen (fatty acid), an aliphatic group (fatty monoester) or a metal ion (carboxylate salt);

n1 is an integer equal to or greater than 0 (typically 0 to 6; more typically 0, 3, 6);

n3 is an integer equal to or greater than 0 (typically 1); and x is an integer equal to or greater than 2 (typically 2 to 6, more typically 2 to 3).

In exemplary embodiments, the Δ9 polyunsaturated starting materials have a total of 18 carbons in the alkene chain. Examples include $CH_3$—$(CH_2)_4$—CH═CH—$CH_2$—CH═CH—$(CH_2)_7$—COOR; and $CH_3$—$CH_2$—CH═CH—$CH_2$—CH═CH—$CH_2$—CH═CH—$(CH_2)_7$—COOR.

where R is hydrogen (fatty acid), an aliphatic group (fatty monoester) or a metal ion (fatty acid salt);

Δ9 unsaturated fatty esters may be monoesters or polyol esters. In many embodiments, the Δ9 unsaturated polyol esters have the general structure $CH_2A$-$CHB$—$CH_2C$ where -A; —B; and —C are independently selected from

—OH;

—O(O)C—R'; and

—O(O)C—$(CH_2)_7$—[—CH═CH—$CH_2$—$]_x$—$(CH_2)_{n1}CH_3$ with the proviso that at least one of -A, —B, or —C is —O(O)C—$(CH_2)_7$—[—CH═CH—$CH_2$—$]_x$—$(CH_2)_{n1}CH_3$ In the above formula:

R' is a straight or branched chain alkyl or alkenyl group;

n1 is independently an integer equal to or greater than 0 (typically 0 to 6); and x is an integer greater than or equal to 2 (typically 2 to 6, more typically 2 to 3).

In exemplary embodiments, the starting composition comprises one or more C18 fatty acids, for example, linoleic acid (i.e., 9,12-octadecadienoic acid) and linolenic acid (i.e., 9,12, 15-octadecatrienoic acid). In other exemplary embodiments, the starting composition comprises one or more C18 fatty esters, for example, methyl linoleate and methyl linolenate. In yet another exemplary embodiment, the starting composition comprises an unsaturated glyceride comprising Δ9 fatty acids, for example, C18:Δ9 fatty acids.

Δ9 starting compositions may be derived, for example, from vegetable oils such as soybean oil, rapeseed oil, corn oil, sesame oil, cottonseed oil, sunflower oil, canola oil, safflower oil, palm oil, palm kernel oil, linseed oil, castor oil, olive oil, peanut oil, and the like. Since these vegetable oils yield predominately the glyceride form of the Δ9 unsaturated fatty esters, the oils must be processed (e.g., by transesterification) to yield an unsaturated free fatty ester, an unsaturated fatty acid, or salt. Δ9 unsaturated fatty acids, esters, and salts may also be also be derived from tall oil, fish oil, lard, and tallow. A summary of some useful starting compositions is provided in TABLE B.

TABLE B

| Starting Composition | Description | Classification | Bond Locations |
|---|---|---|---|
| Linoleic acid | C18 diunsaturated fatty acid (C18:2) | Δ9 | Δ9, 12 |
| Linolenic acid | C18 triunsaturated fatty acid (C18:3) | Δ9 | Δ9, 12, 15 |
| Alkyl linoleate | C18 diunsaturated fatty ester (C18:2) | Δ9 | Δ9, 12 |
| Alkyl linolenate | C18 triunsaturated fatty ester (C18:3) | Δ9 | Δ9, 12, 15 |
| Vegetable Oil (e.g., soybean oil) | Unsaturated glycerides of C18:1, C18:2, and C18:3 fatty acids | Δ9 | Δ9<br>Δ9, 12<br>Δ9, 12, 15 |

Metathesis involves the interchange of alkylidene units among olefinic hydrocarbons via the formation and cleavage of carbon-carbon double bonds. The multiple unsaturated bonds within one polyunsaturated fatty acid or fatty ester thus provide multiple reaction sites for metathesis. Multiple reaction sites exponentially increase the chemical identity of metathesis reaction products, which in turn increases the complexity of the metathesis product composition. Multiple reaction sites within the starting material can also increase the catalyst demand for the reaction. These factors can increase the overall complexity and inefficiency of the metathesis reaction.

The inventive method(s) can be used to provide a more efficient metathesis process that can reduce catalyst demand and reduce complexity of the reaction product composition. The inventive methods utilize a hydrogenation reaction prior to metathesis, wherein hydrogenation reduces the polyunsaturated groups within the starting material. The hydrogenation product composition can then be subjected to metathesis to provide a second composition comprising a mixture of metathesis products. In some embodiments, the metathesis products are fatty esters (monoesters or polyol esters) having terminal carbon-carbon double bonds. The fatty esters may be hydrolyzed to yield linear fatty acids having terminal carbon-carbon double bonds. In some embodiments, the linear fatty acids with terminal carbon-carbon double bonds are monounsaturated. In some embodiments, the terminal linear fatty acids have a chain length in the range of 3 to n carbon atoms (where n is the chain length of the partially hydrogenated composition which has a double bond at the 2 to (n−1) position after partial hydrogenation). In other embodiments, the terminal fatty acids have a chain length in the range of 5 to (n−1) carbon atoms (where n is the chain length of the partially hydrogenated composition which has a double bond at the 4 to (n−2) position after partial hydrogenation). In exemplary embodiments, the terminal fatty acids have a chain length in the range of 5 to 17 carbon atoms. In other aspects, the metathesis products are monounsaturated diesters having a chain length in the range of 4 to (2n−2) carbon atoms (where n is the chain length of the partially hydrogenated composition, which has a double bond at the 2 to (n−1) position after partial hydrogenation). In other embodiments, the monounsaturated diesters have a chain length in the range of 8 to (2n−4) carbon atoms (where n is the chain length of the partially hydrogenated composition which has a double bond at the 4 to (n−2) position after partial hydrogenation). In exemplary embodiments, the monounsaturated diesters have a chain length in the range of 8 to 32 carbon atoms. Such metathesis products can be particularly useful, as discussed herein.

For purposes of illustration, the inventive methods will be described with reference to soybean oil as an exemplary starting material. Generally, crude soybean oil includes about 95-97 wt % triacylglycerides, while refined oil contains about 99 wt % or greater triacylglycerides. Free fatty acids comprise less than about 1 wt % of crude soybean oil, and less than 0.05 wt % of refined soybean oil. Generally speaking, the five major fatty acids present in soybean oil are linolenic (C18:3), linoleic (C18:2), oleic (C18:1), stearic (C18:0) and palmitic (C16:0). The relative amounts of the component fatty acids can vary widely, especially for unsaturated fatty acid. Illustrative ranges for the major fatty acids are as follows: linolenic (2-13 wt %), linoleic (35-60 wt %), oleic (20-50 wt %), stearic (2-5.5 wt %) and palmitic (7-12 wt %). Because of the high unsaturated acid content of soybean oil, nearly all of the glyceride molecules contain at least 2 unsaturated fatty acids. It will be understood that the inventive methods can utilize other polyunsaturated fatty acids, polyunsaturated fatty monoesters, polyunsaturated polyol esters, or mixtures thereof in accordance with the described principles.

Partial Hydrogenation

The inventive method(s) involve subjecting a polyunsaturated fatty acid composition to partial hydrogenation. In accordance with the invention, polyunsaturated compositions are partially hydrogenated under conditions to optimize the composition for metathesis. Preferably, the methods involve partial hydrogenation of the polyunsaturated composition. Partial hydrogenation of the polyunsaturated fatty acid composition reduces the number of double bonds that are available to participate in a subsequent metathesis reaction.

Partial hydrogenation can also alter the fatty acid composition of the polyunsaturated fatty acid composition. Positional and/or geometrical isomerization can occur during hydrogenation, thus changing the location and/or orientation of the double bonds. It is believed these reactions typically occur concurrently. In the geometrical isomers, the cis bonds originally present in naturally occurring soybean oil are converted in part to the trans form.

Partial hydrogenation can be conducted according to any known method for hydrogenating double bond-containing compounds such as vegetable oils. Catalysts for hydrogenation are known and can be homogeneous or heterogeneous (e.g., present in a different phase, typically the solid phase, than the substrate). One useful hydrogenation catalyst is nickel. Other useful hydrogenation catalysts include copper, palladium, platinum, molybdenum, iron, ruthenium, osmium, rhodium, iridium, zinc or cobalt. Combinations of catalysts can also be used. Bimetallic catalysts can be used, for example, palladium-copper, palladium-lead, nickel-chromite.

The metal catalysts can be utilized with promoters that may or may not be other metals. Illustrative metal catalysts with promoter include, for example, nickel with sulfur or copper as promoter; copper with chromium or zinc as promoter; zinc with chromium as promoter; or palladium on carbon with silver or bismuth as promoter.

In some embodiments, the polyunsaturated composition is partially hydrogenated in the presence of a nickel catalyst that has been chemically reduced with hydrogen to an active state. Commercial examples of supported nickel hydrogenation catalysts include those available under the trade designations "NYSOFACT," "NYSOSEL," AND "NI 5248 D" (from Engelhard Corporation, Iselin, N.J.). Additional supported nickel hydrogenation catalysts include those commercially available under the trade designations "PRICAT 9910," "PRICAT 9920," "PRICAT 9908" and "PRICAT 9936" (from Johnson Matthey Catalysts, Ward Hill, Mass.).

In some aspects, the metal catalysts can be used as fine dispersions in a hydrogenation reaction (slurry phase environment). For example, in some embodiments, the particles of supported nickel catalyst are dispersed in a protective medium comprising hardened triacylglyceride, edible oil, or tallow. In an exemplary embodiment, the supported nickel catalyst is dispersed in the protective medium at a level of about 22 wt % nickel.

In some aspects, the catalysts can be impregnated on solid supports. Some useful supports include carbon, silica, alumina, magnesia, titania, and zirconia, for example. Illustrative support embodiments include, for example, palladium, platinum, rhodium or ruthenium on carbon or alumina support; nickel on magnesia, alumina or zirconia support; palladium on barium sulfate ($BaSO_4$) support; or copper on silica support.

In some embodiments, the catalysts are supported nickel or sponge nickel type catalysts. In some embodiments, the hydrogenation catalyst comprises nickel that has been chemically reduced with hydrogen to an active state (i.e., reduced nickel) provided on a support. In some embodiments, the support comprises porous silica (e.g., kieselguhr, infusorial, diatomaceous, or siliceous earth) or alumina. The catalysts are characterized by a high nickel surface area per gram of nickel.

In some embodiments, the supported nickel catalysts are of the type reported in U.S. Pat. No. 3,351,566 (Taylor et al.). These catalysts comprise solid nickel-silica having a stabilized high nickel surface area of 45 to 60 sq. meters per gram and a total surface area of 225 to 300 sq. meters per gram. The catalysts are prepared by precipitating the nickel and silicate ions from solution such as nickel hydrosilicate onto porous silica particles in such proportions that the activated catalyst contains 25 wt % to 50 wt % nickel and a total silica content of 30 wt % to 90 wt %. The particles are activated by calcining in air at 600° F. to 900° F. (315.5° C. to 482.2° C.), then reducing with hydrogen.

Useful catalysts having a high nickel content are described in EP 0 168 091, wherein the catalyst is made by precipitation of a nickel compound. A soluble aluminum compound is added to the slurry of the precipitated nickel compound while the precipitate is maturing. After reduction of the resultant catalyst precursor, the reduced catalyst typically has a nickel surface area on the order of 90 to 150 sq. meters per gram of total nickel. The catalysts have a nickel/aluminum atomic ratio in the range of 2 to 10 and have a total nickel content of more than about 66% by weight.

Useful high activity nickel/alumina/silica catalysts are described in EP 0 167 201. The reduced catalysts have a high nickel surface area per gram of total nickel in the catalyst.

Useful nickel/silica hydrogenation catalysts are described in U.S. Pat. No. 6,846,772 (Lok et al.). The catalysts are produced by heating a slurry of particulate silica (e.g., kieselguhr) in an aqueous nickel amine carbonate solution for a total period of at least 200 minutes at a pH above 7.5, followed by filtration, washing, drying, and optionally calcination. The nickel/silica hydrogenation catalysts are reported to have improved filtration properties. U.S. Pat. No. 4,490,480 (Lok et al.) reports high surface area nickel/alumina hydrogenation catalysts having a total nickel content of 5% to 40% by weight.

The amount of hydrogenation catalysts is typically selected in view of a number of factors including, for example, the type of hydrogenation catalyst(s) used, the degree of unsaturation in the material to be hydrogenated, the desired rate of hydrogenation, the desired degree of hydrogenation (for example, as measured by the IV, see below), the purity of the reagent and the $H_2$ gas pressure. In some embodiments, the hydrogenation catalyst is used in an amount of about 10 wt % or less, for example about 5 wt % or less, about 1 wt % or less, or about 0.5 wt % or less.

Partial hydrogenation can be carried out in a batch, continuous or semi-continuous process. In a representative batch process, a vacuum is pulled on the headspace of a stirred reaction vessel and the reaction vessel is charged with the material to be hydrogenated (for example, RBD soybean oil). The material is then heated to a desired temperature, typically in the range of about 50° C. to about 350° C., for example, about 100° C. to about 300° C., or about 150° C. to about 250° C. The desired temperature can vary, for example, with hydrogen gas pressure. Typically, a higher gas pressure will require a lower temperature. In a separate container, the hydrogenation catalyst is weighed into a mixing vessel and is slurried in a small amount of the material to be hydrogenated (for example, RBD soybean oil). When the material to be hydrogenated reaches the desired temperature (typically a temperature below a target hydrogenation temperature), the slurry of hydrogenation catalyst is added to the reaction vessel. Hydrogen is then pumped into the reaction vessel to achieve a desired pressure of $H_2$ gas. Typically, the $H_2$ gas pressure ranges from about 15 psig to about 3000 psig, for example, about 15 psig to about 90 psig. As the gas pressure increases, more specialized high-pressure processing equipment can be required. Under these conditions the hydrogenation reaction begins and the temperature is allowed to increase to the desired hydrogenation temperature (for example, about 120° C. to about 200° C.), where it is maintained by cooling the reaction mass, for example, with cooling coils. When the desired degree of hydrogenation is reached, the reaction mass is cooled to the desired filtration temperature.

The polyunsaturated composition can be subjected to electrocatalytic hydrogenation to achieve a partially hydrogenated product. Various electrocatalytic hydrogenation processes can be utilized in accordance with the invention. For example, low temperature electrocatalytic hydrogenation that uses an electrically conducting catalyst such as Raney Nickel or Platinum black as a cathode are described in Yusem and Pintauro, *J. Appl. Electrochem.* 1997, 27, 1157-71. Another system that utilizes a solid polymer electrolyte reactor composed of a ruthenium oxide ($RuO_2$) powder anode and a platinum-black (Pt-black) or palladium-black (Pd-black) powder cathode that are hot-pressed as thin films onto a Nafion cation exchange membrane is described in An et al. *J. Am. Oil Chem. Soc.* 1998, 75,917-25. A further system that involves electrochemical hydrogenation using a hydrogen transfer agent of formic acid and a nickel catalyst is described in Mondal and Lalvani, *J. Am. Oil Chem. Soc.* 2003, 80, 1135-41.

In further aspects, hydrogenation can be performed under supercritical fluid state, as described in U.S. Pat. No. 5,962,711 (Härröd et al., Oct. 5, 1999) and U.S. Pat. No. 6,265,596 (Härröd et al., Jul. 24, 2001), described in more detail infra.

In preferred aspects, hydrogenation is conducted in a manner to promote selectivity toward monounsaturated fatty acid groups, i.e., fatty acid groups containing a single carbon-carbon double bond. Selectivity is understood here as the tendency of the hydrogenation process to hydrogenate polyunsaturated fatty acid groups over monounsaturated fatty acid groups. This form of selectivity is often called preferential selectivity, or selective hydrogenation.

The level of selectivity of hydrogenation can be influenced by the nature of the catalyst, the reaction conditions, and the presence of impurities. Generally speaking, catalysts having a high selectivity in one fat or oil also have a high selectivity in other fats or oils. As used herein, "selective hydrogenation" refers to hydrogenation conditions (e.g., selection of catalyst, reaction conditions such as temperature, rate of heating and/or cooling, catalyst concentration, hydrogen availability, and the like) that are chosen to promote hydrogenation of polyunsaturated compounds to monounsaturated compounds. Using soybean oil as an example, the selectivity of the hydrogenation process is determined by examining the content of the various C18 fatty acids and their ratios. Hydrogenation on a macro scale can be regarded as a stepwise process:

$$C18{:}3 \xrightarrow{k_3} C18{:}2 \xrightarrow{k_2} C18{:}1 \xrightarrow{k_1} C18{:}0$$

The following selectivity ratios (SR) can be defined: $SRI=k_2/k_3$; $SRII=k_3/k_2$; $SRIII=k_2/k_1$. Characteristics of the starting oil and the hydrogenated product are utilized to determine the selectivity ratio (SR) for each acid. This is typically done with the assistance of gas-liquid chromatography. For example, polyol esters may be saponified to yield free fatty acids (FFA) by reacting with NaOH/MeOH. The FFAs are then methylated into fatty acid methyl esters (FAMEs) using $BF_3$/MeOH as the acid catalyst and MeOH as the derivatization reagent. The resulting FAMEs are then separated using a gas-liquid chromatograph and are detected with a flame ionization detector (GC/FID). An internal standard is used to determine the weight percent of the fatty esters. The rate constants can be calculated by either the use of a computer or graph, as is known.

In addition to the selectivity ratios, the following individual reaction rate constants can be described within the hydrogenation reaction: $k_3$ (C18:3 to C18:2), $k_2$ (C18:2 to C18:1), and $k_1$ (C18:1 to C18:0). In some aspects, the inventive method involves hydrogenation under conditions sufficient to provide a selectivity or preference for $k_2$ and/or $k_3$ (i.e., $k_2$ and/or $k_3$ are greater than $k_1$). In these aspects, then, hydrogenation is conducted to reduce levels of polyunsaturated compounds within the starting material, while minimizing generation of saturated compounds.

In one illustrative embodiment, selective hydrogenation can promote hydrogenation of polyunsaturated fatty acid groups toward monounsaturated fatty acid groups (having one carbon-carbon double bond), for example, tri- or diunsaturated fatty acid groups to monounsaturated groups. In some embodiments, the invention involves selective hydrogenation of a polyunsaturated polyol ester (such as soybean oil) to a hydrogenation product having a minimum of 65% monounsaturated fatty acid groups, or a minimum of 75% monounsaturated fatty acid groups, or a minimum of 85% monounsaturated fatty acid groups. It is understood the target minimum percentage of monounsaturated fatty acid groups will depend upon the starting composition (i.e., the polyunsaturated polyol ester), since each polyol ester will have different starting levels of saturates, monounsaturates and polyunsaturates. It is also understood that high oleic oils can have 80% or more oleic acid. In such cases, very little hydrogenation will be required to reduce polyunsaturates.

In one illustrative embodiment, selective hydrogenation can promote hydrogenation of polyunsaturated fatty acid groups in soybean oil toward C18:1, for example, C18:2 to C18:1, and/or C18:3 to C18:2. In some aspects, the invention involves selective hydrogenation of a polyunsaturated composition (e.g., a polyol ester such as SBO) to a hydrogenation product having reduced polyunsaturated fatty acid group content, while minimizing complete hydrogenation to saturated fatty acid groups (C18:0).

Selective hydrogenation in accordance with the invention can be accomplished by controlling reaction conditions (such as temperature, rate of heating and/or cooling, hydrogen availability, and catalyst concentration), and/or by selection of catalyst. For some hydrogenation catalysts, increased temperature or catalyst concentration will result in an increased selectivity for hydrogenating C18:2 over C18:1. In some aspects, when a nickel-supported catalyst is utilized, pressure and/or temperature can be modified to provide selectivity. Illustrative lower pressures can include pressures of 50 psi or less. Lower pressures can be combined, in some embodiments, with increased temperature to promote selectivity. Illustrative conditions in accordance with these embodiments include temperatures in the range of 180° C. to 220° C., pressure of about 5 psi, with nickel catalyst present in an amount of about 0.5 wt %. See, for example, Allen et al. "*Isomerization During Hydrogenation. III. Linoleic Acid,*" *JAOC* August 1956.

In some aspects, selectivity can be enhanced by diminishing the availability of hydrogen. For example, reduced reaction pressure and/or agitation rate can diminish hydrogen supply for the reaction.

Selective hydrogenation can be accomplished by selection of the catalyst. One illustrative catalyst that can enhance selectivity is palladium. Palladium reaction conditions for sunflower oil can include low temperatures (e.g., 40° C.) in ethanol solvent, with catalyst present in an amount of about 1 wt %. Palladium can be provided on a variety of different supports known for hydrogenation processes. See, for example, Bendaoud Nohaira et al., *Palladium supported catalysts for the selective hydrogenation of sunflower oil," J. of Molecular Catalysts A: Chemical* 229 (2005) 117-126. Nov. 20, 2004.

Optionally, additives such as lead or copper can be included to increase selectivity. When catalysts containing palladium, nickel or cobalt are used, additives such as amines can be used.

Useful selective hydrogenation conditions are described, for example, in U.S. Pat. No. 5,962,711 (Härröd et al., Oct. 5, 1999) and U.S. Pat. No. 6,265,596 (Härröd et al., Jul. 24, 2001). Hydrogenation is performed by mixing the substrate (polyunsaturated polyol ester), hydrogen gas and solvent, and bringing the whole mixture into a super-critical or near-critical state. This substantially homogeneous super-critical or near-critical solution is led over the catalyst, whereby the reaction products formed (i.e., the hydrogenated substrates) will also be a part of the substantially homogeneous super-critical or near-critical solution. At partial hydrogenation the reaction is interrupted at a certain desired IV (see below).

Reaction conditions for supercritical hydrogenation may occur over a wide experimental range, and this range can be described as follows: temperature (in the range of about 0° C. to about 250° C. or about 20° C. to about 200° C.); pressure (in the range of about 10 bar to about 350 bar, or about 20 bar to about 200 bar); reaction time (up to about 10 minutes, or in the range of about 1 μsecond to about 1 minute); and solvent concentration (in the range of about 30 wt % to about 99.9 wt %, or about 40 wt % to about 99 wt %). Useful solvents include, for example, ethane, propane, butane, $CO_2$, dimethyl ether, "freons," $N_2O$, $N_2$, $NH_3$, or mixtures of these. The catalyst can be selected according to the reaction to be carried out; any useful catalyst for hydrogenation can be selected. Concentration of hydrogen gas ($H_2$) can be up to 3 wt %, or in the range of about 0.001 wt % to about 1 wt %. Concentration of substrate (polyunsaturated polyol ester) in the reaction mixture can be in the range of about 0.1 wt % to about 70 wt %, or about 1 wt % to about 60 wt %. A continuous reactor can be used to conduct the hydrogenation reaction, such as described in U.S. Pat. No. 5,962,711 (Härröd et al., Oct. 5, 1999) and U.S. Pat. No. 6,265,596 (Härröd et al., Jul. 24, 2001).

In some aspects, content of the starting material may influence the selectivity. In these aspects, various substances that are naturally occurring in fats and oils influence the selectivity of hydrogenation. For example, sulfur is known to be an irreversible surface poison for nickel catalysts. Other compounds that may inhibit catalyst activity include phosphatides, nitrogen and halogen derivatives. As a result, certain embodiments of the invention involve a refining step to remove substances that may have a net negative impact on the hydrogenation process. This, in turn, may increase selectivity.

Partial Hydrogenation Product

Products of the partial hydrogenation reaction can include one or more identifiable properties and/or compounds. Products formed from polyunsaturated compositions can include characteristic monounsaturated fatty acid groups in an acid profile and can contain minor amounts of polyunsaturated fatty acid groups. In some aspects, the acid profile comprises polyunsaturated fatty acid groups in an amount of about 1 wt % or less. In some aspects, the starting material is SBO, and the acid profile of the hydrogenation product comprises a majority of monounsaturated fatty acid groups having a carbon-carbon double bond in the C4 to C16 position on the fatty acid or ester. More generally speaking, the carbon-carbon double bond is located on the fatty acid or ester in the C2 to C(n−1) position, where n is the chain length of the fatty acid or ester. More typically, the carbon-carbon double bond is located on the fatty acid or ester in the C4 to C(n−2), where n is the chain length of the fatty acid or ester. Typically, n ranges from about 4 to about 30, in some embodiments from about 4 to 22.

In further aspects, when the starting material is derived from SBO, the acid profile of the partial hydrogenation product composition comprises saturated fatty acid groups in an amount that is slightly higher than the starting concentration of saturated fatty acid groups in the starting material (i.e., unhydrogenated polyunsaturated polyol ester). In some aspects, the acid profile of the partial hydrogenation product composition comprises saturated fatty acid groups in an amount of about 0.5 wt % to about 10 wt % higher than the concentration of saturated fatty acid groups in the starting material (polyunsaturated polyol ester starting material). In some aspects, the acid profile of the partial hydrogenation product composition comprises saturated fatty acid groups in an amount of about 0.5 wt % to about 6 wt % higher than the concentration of saturated fatty acid groups in the starting material. It is understood that partial hydrogenation will typically result in generation of some additional saturated fatty acid groups. Preferably, the generation of such additional saturated fatty acid groups is controlled through selectivity. Generally speaking, saturated fatty acid groups will not participate in a subsequent metathesis reaction and thus can represent yield loss.

As one example of a partial hydrogenation product composition, when the starting material comprises soybean oil, a partial hydrogenation product composition can include saturated fatty acid groups in an amount of about 30 wt % or less, or 25 wt % or less, or 20 wt % or less. In some aspects, the acid profile can comprise saturated fatty acid groups in an amount in the range of about 15 wt % to about 20 wt %. For soybean oil, illustrative saturated fatty acid groups include stearic and palmitic acids. It is understood the relative amount and identity of the saturated fatty acids within the partial hydrogenated product composition can vary, depending upon such factors as the starting material (polyunsaturated polyol ester), reaction conditions (including catalyst, temperature, pressure, and other factors impacting selectivity of hydrogenation), and positional isomerization. A representative example of a hydrogenation product from selective hydrogenation of SBO is shown in TABLE C below.

TABLE C

Percentages of Octadecenoates from Partially Hydrogenated SBO (C18:1 for SBO-693).

| Relative Percent | Proposed C18:1 Compounds |
|---|---|
| 0.09 | C18:1,4t |
| 0.23 | C18:1,5t |
| 6.01 | C18:1,6-8t |
| 5.88 | C18:1,9t |
| 9.75 | C18:1,10t |
| 8.64 | C18:1,11t |
| 4.89 | C18:1,12t |
| 6.62 | C18:1,13t + 14t (C18:1,6-8c) |
| 14.00 | C18:1,9c (Oleic) (C18:1,14-16t) |
| 3.64 | C18:1,10c (C18:1,15t) |
| 3.00 | C18:1,11c |

TABLE C-continued

| Percentages of Octadecenoates from Partially Hydrogenated SBO (C18:1 for SBO-693). | |
|---|---|
| Relative Percent | Proposed C18:1 Compounds |
| 4.47 | C18:1,12c |
| 1.02 | C18:1,13c |
| 1.16 | C18:1,14c (C18:1,16t) |

Within TABLE C, isomers are indicated as trans ("t") or cis ("c"), with the position of the double bond immediately preceeding the isomer designation. Thus, "4t" is a trans isomer with the double bond at the C4 position within the carbon chain. Species in parenthesis denote minor products that may be present with similar elution times.

Further, in some of these embodiments, the acid profile of the hydrogenation product composition from soybean oil can comprise at least about 65 wt % monounsaturated fatty acid groups. In some embodiments, the acid profile of the hydrogenation product composition can comprise at least about 70 wt %, or at least about 75 wt %, or at least about 80 wt %, or at least about 85 wt % monounsaturated fatty acid groups. The monounsaturated fatty acid groups can include the carbon-carbon double bond at any position from C2 to C16. Using soybean oil as an example, the monounsaturated fatty acid groups of the fatty acid profile can include the following:

octadec-2-enoic acid ($—OOCCH═CH(CH_2)_{14}CH_3$), octadec-3-enoic acid ($—OOC(CH_2)CH═CH(CH_2)_{13}CH_3$), octadec-4-enoic acid ($—OOC(CH_2)_2CH═CH(CH_2)_{12}CH_3$), octadec-5-enoic acid ($—OOC(CH_2)_3CH═CH(CH_2)_{11}CH_3$), octadec-6-enoic acid ($—OOC(CH_2)_4CH═CH(CH_2)_{10}CH_3$), octadec-7-enoic acid ($—OOC(CH_2)_5CH═CH(CH_2)_9CH_3$), octadec-8-enoic acid ($—OOC(CH_2)_6CH═CH(CH_2)_8CH_3$), octadec-9-enoic acid ($—OOC(CH_2)_7CH═CH(CH_2)_7CH_3$), octadec-10-enoic acid ($—OOC(CH_2)_8CH═CH(CH_2)_6CH_3$), octadec-11-enoic acid ($—OOC(CH_2)_9CH═CH(CH_2)_5CH_3$), octadec-12-enoic acid ($—OOC(CH_2)_{10}CH═CH(CH_2)_4CH_3$), octadec-13-enoic acid ($—OOC(CH_2)_{11}CH═CH(CH_2)_3CH_3$), octadec-14-enoic acid ($—OOC(CH_2)_{12}CH═CH(CH_2)_2CH_3$), octadec-15-enoic acid ($—OOC(CH_2)_{13}CH═CH(CH_2)_1CH_3$), octadec-16-enoic acid ($—OOC(CH_2)_{14}CH═CHCH_3$), and For each monounsaturated fatty acid, the fatty acid can be the cis or trans isomer.

The major objective of selective hydrogenation is reduction in the amount of polyunsaturated fatty acid groups of the polyunsaturated composition (e.g., polyunsaturated polyol ester). In some embodiments, the hydrogenation product composition has a polyunsaturated fatty acid group content of about 10 wt % or less, based upon total fatty acid content in the composition. Particularly with respect to hydrogenation product that is to be subjected to self-metathesis, hydrogenation can be performed to drive down the concentration of polyunsaturated fatty acid groups even lower than 5 wt %, for example to concentrations of about 1 wt % or less, or about 0.75 wt % or less, or about 0.5 wt % or less.

The hydrogenation product composition thus comprises a reduced polyunsaturate content relative to the polyunsaturated starting material. In some aspects, the hydrogenation product composition can comprise polyunsaturated fatty acid groups in an amount of about 1 wt % or less; saturated fatty acid groups in an amount in the range of about 30 wt % or less, or about 25 wt % or less, or about 20 wt % or less; and monounsaturated fatty acid groups comprising the balance of the mixture, for example, about 65 wt % or more, or about 70 wt % or more, or about 75 wt % or more, or about 80 wt % or more, or about 85 wt % or more. This product composition is understood to be illustrative for soybean oil, and it is understood the relative amounts of each level of saturated, monounsaturated and polyunsaturated components could vary depending upon such factors as the starting material (e.g., polyunsaturated polyol ester), the hydrogenation catalyst selected, the hydrogenation reaction conditions, and the like factors described herein.

Generally, it is desirable to maximize the concentration of monounsaturated fatty acid groups in the hydrogenation product composition. In many embodiments, the monounsaturated fatty acid groups comprise monounsaturated fatty acid groups having the carbon-carbon double bond in the C4 to C16 position within the carbon chain.

The hydrogenation product composition thus comprises a partially hydrogenated polyol ester. As mentioned previously, in addition to effecting a reduction of unsaturation of the polyol ester, partial hydrogenation can also cause geometric and positional isomers to be formed. The primary goal of selective hydrogenation, in accordance with principles of the invention, is reduction in the amount of polyunsaturation in the polyol esters, and positional and/or geometric (particularly geometric) isomerization is not a primary concern.

The hydrogenation product composition can also be characterized as having an iodine value (IV, also referred to as the iodine number) within a desired range. The IV is a measure of the degree of unsaturation of a compound. The IV measures the amount of iodine absorbed by a fixed weight of a compound or mixture. When used in reference to an unsaturated material, such as an unsaturated polyol ester, the IV is thus a measure of the unsaturation, or the number of double bonds, of that compound or mixture. Obtaining the IV for a compound or mixture is a well-known procedure and will not be further described herein.

Generally speaking, the IV can range from 8 to 180 in naturally-occurring seed oils and 90 to 210 in naturally-occurring marine oils. Illustrative IV for some natural oils is as follows:

| Oil | IV |
|---|---|
| soy | 125-138 |
| canola | 110-115 |
| palm | 45-56 |
| rapeseed | 97-110 |
| sunflower | 122-139 |
| fish | 115-210 |

At complete hydrogenation of oils or fats, all double bonds would be hydrogenated and the IV is therefore near zero. For partially hydrogenated triglycerides in accordance with the invention, the IV value can be about 90 or lower, or about 85 or lower, or about 80 or lower, or about 75 or lower. The IV target will depend upon such factors as the initial IV, the content of the monounsaturates in the starting material, the selectivity of the hydrogenation catalyst, the economic optimum level of unsaturation, and the like. An optimum partial hydrogenation would leave only the saturates that were initially present in the polyunsaturated polyol ester starting material and react all of the polyunsaturates. For example, a triolein oil would have an IV of about 86. Soybean oil starts with an IV of around 130 with a saturates content of 15%. An optimum partial hydrogenation product would have an IV of 73 and would maintain the 15% level of saturates. Canola oil has an initial IV of about 113 and 7% saturates; an optimum partial hydrogenation product would have an IV of about 80, while maintaining the 7% saturate level. The balance between additional saturate production and allowable polyunsaturate content can depend upon such factors as product quality parameters, yield costs, catalyst costs, and the like. If catalyst costs dominate, then some saturate production may be tolerable. If yield is critical, then some remaining polyunsaturates may be tolerable. If the formation of cyclic byproducts is unacceptable, then it may be acceptable to drive polyunsaturate levels to near zero.

The IV can represent a hydrogenation product composition wherein a certain percentage of double bonds have reacted, on a molar basis, based upon the starting IV of the polyunsaturated composition. In some aspects, the invention involves a starting material that is an SBO having an IV of 130.

After partial hydrogenation, the hydrogenation catalyst can be removed from the partial hydrogenated product using known techniques, for example, by filtration. In some embodiments, the hydrogenation catalyst is removed using a plate and frame filter such as those commercially available from Sparkle Filters, Inc., Conroe, Tex. In some embodiments, the filtration is performed with the assistance of pressure or a vacuum. In order to improve filtering performance, a filter aid can optionally be used. A filter aid can be added to the hydrogenated product directly or it can be applied to the filter. Representative examples of filtering aids include diatomaceous earth, silica, alumina and carbon. Typically, the filtering aid is used in an amount of about 10 wt % or less, for example, about 5 wt % or less, or about 1 wt % or less. Other filtering techniques and filtering aids can also be employed to remove the used hydrogenation catalyst. In other embodiments, the hydrogenation catalyst is removed by using centrifugation followed by decantation of the product.

Partial hydrogenation of a polyunsaturated composition can impart one or more desirable properties to the partially hydrogenated composition and, consequently, to metathesis processes performed on the partially hydrogenated composition. For example, partial hydrogenation can be used to decrease the amount of polyunsaturated fatty acid groups in the composition, thereby reducing unneeded sites of reaction for a metathesis catalyst. This, in turn, can reduce catalyst demand. Another benefit can be seen in the final metathesis product composition. Because less polyunsaturated fatty acid groups are present in the reaction mixture prior to metathesis, a more predictable metathesis product composition can be provided. For example, the carbon chain length and double bond position of metathesis products can be predicted, based upon the fatty acid composition and metathesis catalyst utilized. This, in turn, can reduce the purification requirements for the metathesis product composition. These benefits are discussed further vide infra.

Metathesis

In accordance with the invention, the hydrogenation product composition is subjected to a metathesis reaction. Metathesis is a catalytic reaction that involves the interchange of alkylidene units among compounds containing one or more double bonds (i.e., olefinic compounds) via the formation and cleavage of the carbon-carbon double bonds. Metathesis can occur between two of the same molecules (often referred to as self-metathesis) and/or it can occur between two different molecules (often referred to as cross-metathesis).

Self-metathesis may be represented generally as shown in Equation I.

$$R^1—HC{=}CH—R^2+R^1—CH{=}CH—R^2 \leftrightarrow R^1—CH{=}CH—R^1+R^2—CH{=}CH—R^2 \quad (I)$$

where $R^1$ and $R^2$ are organic groups.

Cross-metathesis may be represented generally as shown in Equation II.

$$R^1—HC{=}CH—R^2+R^3—HC{=}CH—R^4 \leftrightarrow R^1—HC{=}CH—R^3+R^1—HC{=}CH—R^4+R^2—HC{=}CH—R^3+R^2—HC{=}CH—R^4+R^1—HC{=}CH—R^1+R^2—HC{=}CH—R^2+R^3—HC{=}CH—R^3+R^4—HC{=}CH—R^4 \quad (II)$$

where $R^1$, $R^2$, $R^3$, and $R^4$ are organic groups.

When an unsaturated polyol ester comprises molecules having more than one carbon-carbon double bond, self-metathesis results in oligomerization of the starting material. For example, reaction sequence (III) depicts metathesis oligomerization of a representative species (e.g., an unsaturated polyol ester) having more than one carbon-carbon double bond. In reaction sequence (III), the self-metathesis reaction results in the formation of metathesis dimers, metathesis trimers, and metathesis tetramers. Although not shown, higher order oligomers such as metathesis pentamers and metathesis hexamers may also be formed. A metathesis dimer refers to a compound formed when two unsaturated polyol ester molecules are covalently bonded to one another by a metathesis reaction. In many embodiments, the molecular weight of the metathesis dimer is greater than the molecular weight of the unsaturated polyol ester from which the dimer is formed. A metathesis trimer refers to a compound formed when three unsaturated polyol ester molecules are covalently bonded together by metathesis reactions. Typically, a metathesis trimer is formed by the cross-metathesis of a metathesis dimer with an unsaturated polyol ester. A metathesis tetramer refers to a compound formed when four polyol ester molecules are covalently bonded together by metathesis reactions. Typically, a metathesis tetramer is formed by the cross-metathesis of a metathesis trimer with an unsaturated polyol ester or formed by the cross-metathesis of two metathesis dimers.

$$R^1—HC{=}CH—R^2—HC{=}CH—R^3+R^1—HC{=}CH—R^2—HC{=}CH—R^3 \leftrightarrow R^1—HC{=}CH—R^2—HC{=}CH—R^2—HC{=}CH—R^3+\text{(other products)(metathesis dimer)}$$

$$R^1—R^2—HC{=}CH—R^2—HC{=}CH—R^3+R^1—HC{=}CH—R^2—HC{=}CH—R^3 \leftrightarrow R^1—HC{=}CH—R^2—HC{=}CH—R^2—HC{=}CH—R^2—HC{=}CH—R^3+\text{(other products)}\ \text{(metathesis trimer)}$$

$$R^1—HC{=}CH—R^2—HC{=}CH—R^2—HC{=}CH—R^2—HC{=}CH—R^3+R^1—HC{=}CH—R^2—HC{=}CH—R^3 \leftrightarrow R^1—HC{=}CH—R^2—HC{=}CH—R^2—HC{=}CH—R^2—HC{=}CH—R^2—HC{=}CH—R^3+\text{(other products)(metathesis tetramer)} \quad (III)$$

where $R^1$, $R^2$, and $R^3$ are organic groups.

In accordance with the invention, hydrogenated polyol ester is subjected to metathesis (self or cross). An exemplary self-metathesis reaction scheme is shown in FIG. 1. The reaction scheme shown in FIG. 1 highlights the reaction of the major fatty acid group component of the hydrogenation product composition (i.e., triacylglycerides having a monounsaturated fatty acid group). As shown in FIG. 1, a triglyceride having a monounsaturated fatty acid group is self-metathesized in the presence of a metathesis catalyst to form a metathesis product composition. Within FIG. 1 and FIG. 2, the R group designates a diglyceride. In FIG. 1, the reaction composition (18) comprises triglyceride having a monounsaturated fatty acid group. The resulting metathesis product composition includes, as major components, monounsaturated diacid esters in triglyceride form (20), internal olefins (22) and monounsaturated fatty acid esters in triglyceride form (24). Any one or more of the starting material (18) and each of the products shown, 20, 22 and 24, can be present as the cis or trans isomer. Unreacted starting material will also be present (not shown). As illustrated, the metathesis products, 20, 22 and 24 will have overlapping chain lengths. The monounsaturated diacid esters (20) can have utility in forming wax compositions and/or colorant compositions, as described below.

As mentioned earlier, one concern when performing self-metathesis of naturally occurring oils in their triglyceride or other form is the generation light co-products. Here, the naturally occurring methylene interrupted cis, cis configuration can form cyclic compounds that can be present as VOCs. Depending upon the identity and amount of the VOC, it can represent a yield loss and/or a hazardous emission. In some aspects, the inventive methods provide the ability to reduce VOCs during the metathesis phase of the reaction. As the concentration of polyunsaturates is reduced, this in turn reduces the likelihood of generating such metathesis products as cyclohexadienes (e.g., 1,3-cyclohexadiene, 1,4-cyclohexadiene, and the like), which themselves can be VOCs and/or be converted to other VOCs, such as benzene. Thus, in some aspects, the inventive methods can reduce the generation of VOCs and/or control the identity of any yield loss that can result from the metathesis reaction.

In some aspects, then, the invention can provide methods wherein the occurrence of methylene interrupted cis-cis diene structures are reduced in the metathesis reaction mixture. These structures can be converted to other structures by geometric isomerization, positional isomerization, and/or hydrogenation. In turn, these methods can, reduce volatile co-product formation, e.g., in the form of cyclohexadiene. One illustrative method of reducing formation of exemplary volatile co-products (1,3-cyclohexadiene, 1,4-cyclohexadiene and/or benzene) is shown in the examples.

Figure 2:
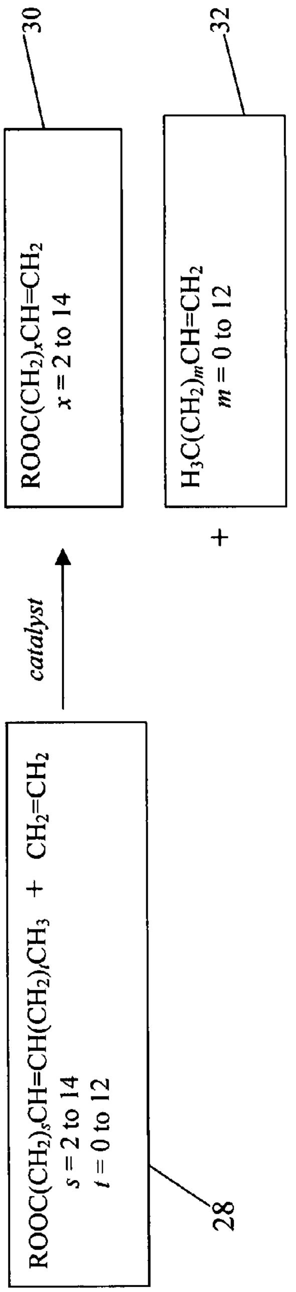
FIG. 2 is an exemplary cross-metathesis reaction scheme.

An exemplary cross-metathesis reaction scheme is illustrated in FIG. 2. As shown in FIG. 2, a triglyceride having a monounsaturated fatty acid group is cross-metathesized with a small olefin (ethylene shown in figure), in the presence of a metathesis catalyst to form a metathesis product composition. As discussed elsewhere herein, acceptable small olefins include, for example, ethylene, propylene, 1-butene, 2-butene, isobutene, 1-pentene, 2-pentene, isopentene, 2-hexene, 3-hexene, and the like.

As shown in FIG. 2, the reaction composition (28) includes triglyceride having a monounsaturated fatty acid group and ethylene. The resulting metathesis product composition includes, as major components, monounsaturated fatty acid esters in triglyceride form having terminal double bonds (30), as well as olefins with terminal double bonds (32). Unreacted starting material can also be present, as well as products from some amount of self-metathesis (not shown in figure). The starting material and each of the products shown, 30 and 32, can be present as the cis or trans isomer (except when ethylene is used in which case the product is a terminal olefin). As illustrated, the metathesis products, 30 and 32 will have overlapping chain lengths. In particular, the chain lengths of the terminal monounsaturated fatty acid esters can be in the range of 5 to 17 carbons. In some aspects, the majority (e.g., 50% or more) of the terminal monounsaturated fatty acids can have chain lengths in the range of 9 to 13 carbon atoms. The monounsaturated fatty acid esters in triglyceride form (30) can have utility in paints and coatings, as well as antimicrobial compositions, as described below.

Metathesis Catalysts

The metathesis reaction is conducted in the presence of a catalytically effective amount of a metathesis catalyst. The term "metathesis catalyst" includes any catalyst or catalyst system which catalyzes the metathesis reaction.

Any known or future-developed metathesis catalyst may be used, alone or in combination with one or more additional catalysts. Exemplary metathesis catalysts include metal carbene catalysts based upon transition metals, for example, ruthenium, molybdenum, osmium, chromium, rhenium, and tungsten. Exemplary ruthenium-based metathesis catalysts include those represented by structures 12 (commonly known as Grubbs's catalyst), 14 and 16, where Ph is phenyl, Mes is mesityl, and Cy is cyclohexyl.

12

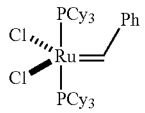

14

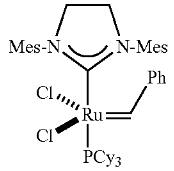

16

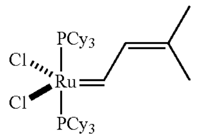

Structures 18, 20, 22, 24, 26, and 28, illustrated below, represent additional ruthenium-based metathesis catalysts, where Ph is phenyl, Mes is mesityl, py is pyridine, Cp is cyclopentyl, and Cy is cyclohexyl. Techniques for using catalysts 12, 14, 16, 18, 20, 22, 24, 26, and 28, as well as additional related metathesis catalysts, are known in the art.

18

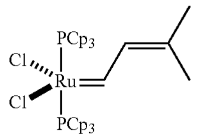

20

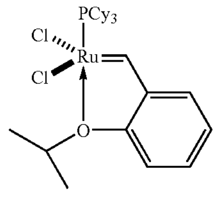

-continued

22

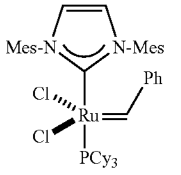

24

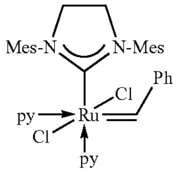

26

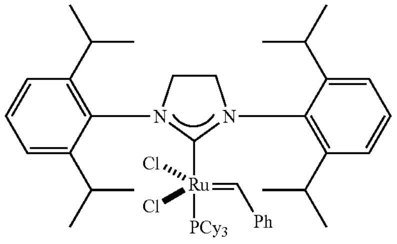

28

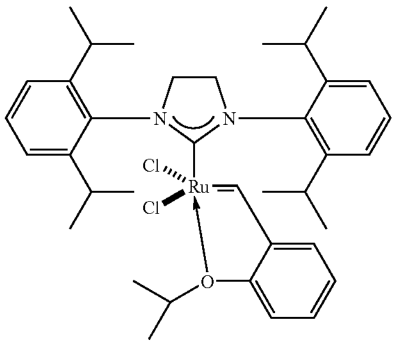

Catalysts C627, C682, C697, C712, and C827 are additional ruthenium-based catalysts, where Cy is cyclohexyl in C827.

C827

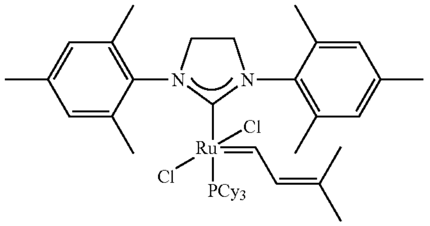

C627

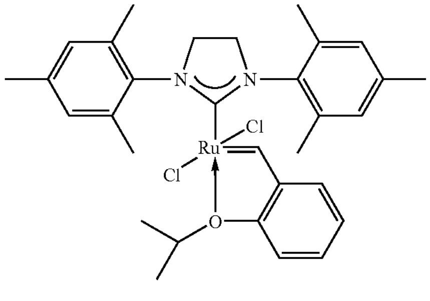

-continued

C712

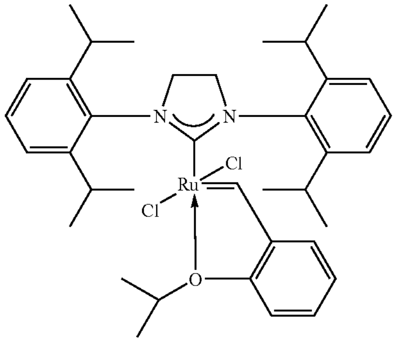

C697

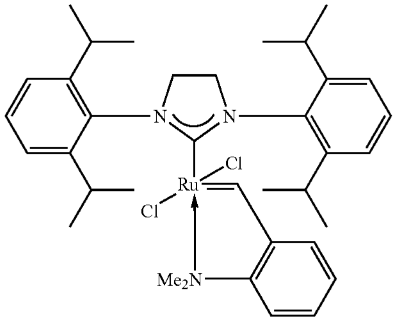

C682

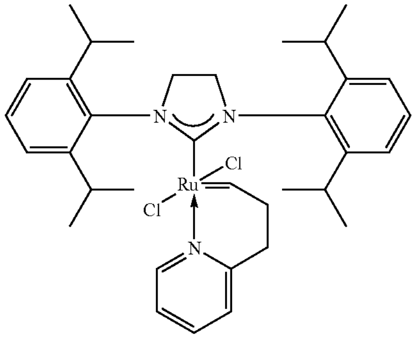

Additional exemplary metathesis catalysts include, without limitation, metal carbene complexes selected from the group consisting of molybdenum, osmium, chromium, rhenium, and tungsten. The term "complex" refers to a metal atom, such as a transition metal atom, with at least one ligand or complexing agent coordinated or bound thereto. Such a ligand typically is a Lewis base in metal carbene complexes useful for alkyne or alkene-metathesis. Typical examples of such ligands include phosphines, halides and stabilized carbenes. Some metathesis catalysts may employ plural metals or metal co-catalysts (e.g., a catalyst comprising a tungsten halide, a tetraalkyl tin compound, and an organoaluminum compound).

An immobilized catalyst can be used for the metathesis process. An immobilized catalyst is a system comprising a catalyst and a support, the catalyst associated with the support. Exemplary associations between the catalyst and the support may occur by way of chemical bonds or weak interactions (e.g. hydrogen bonds, donor acceptor interactions) between the catalyst, or any portions thereof, and the support or any portions thereof. Support is intended to include any material suitable to support the catalyst. Typically, immobilized catalysts are solid phase catalysts that act on liquid or gas phase reactants and products. Exemplary supports are polymers, silica or alumina. Such an immobilized catalyst may be used in a flow process. An immobilized catalyst can simplify purification of products and recovery of the catalyst so that recycling the catalyst may be more convenient.

The metathesis process can be conducted under any conditions adequate to produce the desired metathesis products. For example, stoichiometry, atmosphere, solvent, temperature and pressure can be selected to produce a desired product and to minimize undesirable byproducts. The metathesis process may be conducted under an inert atmosphere. Similarly, if the olefin reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen and combinations thereof.

Similarly, if a solvent is used, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc.

In certain embodiments, a ligand may be added to the metathesis reaction mixture. In many embodiments using a ligand, the ligand is selected to be a molecule that stabilizes the catalyst, and may thus provide an increased turnover number for the catalyst. In some cases the ligand can alter reaction selectivity and product distribution. Examples of ligands that can be used include Lewis base ligands, such as, without limitation, trialkylphosphines, for example tricyclohexylphosphine and tributyl phosphine; triarylphosphines, such as triphenylphosphine; diarylalkylphosphines, such as, diphenylcyclohexylphosphine; pyridines, such as 2,6-dimethylpyridine, 2,4,6-trimethylpyridine; as well as other Lewis basic ligands, such as phosphine oxides and phosphinites. Additives may also be present during metathesis that increase catalyst lifetime.

Any useful amount of the selected metathesis catalyst can be used in the process. For example, the molar ratio of the unsaturated polyol ester to catalyst may range from about 5:1 to about 10,000,000:1 or from about 50:1 to 500,000:1.

The metathesis reaction temperature may be a rate-controlling variable where the temperature is selected to provide a desired product at an acceptable rate. The metathesis temperature may be greater than −40° C., may be greater than about −20° C., and is typically greater than about 0° C. or greater than about 20° C. Typically, the metathesis reaction temperature is less than about 150° C., typically less than about 120° C. An exemplary temperature range for the metathesis reaction ranges from about 20° C. to about 120° C.

The metathesis reaction can be run under any desired pressure. Typically, it will be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than about 10 kPa, in some embodiments greater than about 30 kP, or greater than about 100 kPa. Typically, the reaction pressure is no more than about 7000 kPa, in some embodiments no more than about 3000 kPa. An exemplary pressure range for the metathesis reaction is from about 100 kPa to about 3000 kPa. In some embodiments, it may be desirable to conduct self-metathesis under vacuum conditions, for example, at low as about 0.1 kPa.

In some embodiments, the metathesis reaction is catalyzed by a system containing both a transition and a non-transition metal component. The most active and largest number of catalyst systems are derived from Group VI A transition metals, for example, tungsten and molybdenum.

Hydrolysis, Transesterification, Applications

Optionally, the monounsaturated fatty acid esters in triglyceride form (products 24 and 30 within FIG. 1 and FIG. 2, respectively) can be subjected to hydrolysis to yield linear monounsaturated fatty acids having an internal carbon-carbon double bond (from product 24) or a terminal carbon-carbon double bond (product 30). In yet another embodiment, the monounsaturated fatty acid esters in triglyceride form can be subjected to transesterification with an alcohol to yield an ester of the linear monounsaturated fatty acid, wherein the carbon-carbon double bond is positioned internally on the carbon chain (from product 24) or at a terminal carbon (from product 30). Such hydrolysis and/or transesterification processes are well known in the art.

The resulting linear monounsaturated fatty acids and fatty acid esters can have utility in coatings, as described in WO 2007/092632 (“Surface Coating Compositions And Methods”). The resulting linear monounsaturated fatty acids and fatty acid esters can have utility as antimicrobial compositions as described in WO 2007/092633 (“Antimicrobial Compositions, Methods And Systems”).

In some aspects, the products of metathesis can be utilized to form wax compositions. Wax compositions comprising metathesis products are described in WO 2006/076364 (“Candle and Candle Wax Containing Metathesis and Metathesis-Like Products”) and in International Application No. PCT/US2007/000610 (“Hydrogenated Metathesis Products and Methods of Making”), filed Jan. 10, 2007. In other aspects, the monounsaturated diacid esters (20) resulting from self-metathesis processes can be utilized in colorant compositions as described in WO 2007/103460 (“Colorant Compositions Comprising Metathesized Unsaturated Polyol Esters”).

In addition, the inventive methods can be employed to manufacture other products that are obtained directly or indirectly via metathesis reactions. Representative examples include functionalized polymers (e.g., polyesters), amorphous polymers, industrial chemicals such as additives (e.g., mono- and dicarboxylic acids, surfactants, and solvents).

The invention will now be described with reference to the following non-limiting examples.

EXAMPLES

Example 1

Metathesis of Partially Hydrogenated Soy Oil

Four samples of partially hydrogenated soy oil were obtained and subjected to self-metathesis as follows. Compositional features of the soy oil samples are summarized in TABLE 1:

TABLE 1

| Partially Hydrogenated Soy Oil | | |
|---|---|---|
| Sample | IV | Total polyunsaturates (wt %) |
| A | 120-140 | 61 |
| B | 74.6 | 3.5 |
| C | 79.2 | 8 |
| D | 90.1 | 15.8 |

Sample A was a refined, bleached and deodorized soybean oil (Cargill, Inc.). Samples B through D were partially hydrogenated soybean oils that were obtained by partial hydrogenation of soybean oil using commercially available Nickel catalysts, as follows. The Samples B-D were heated to 350° F., while held under nitrogen, adding 0.4 wt % Ni catalyst to the oil once at 350° F., starting the flow of hydrogen at a pressure of 35 psi, having a hold temperature of about 410° F., and checking the reaction at 1 hour to see where the IV was in comparison to target. After hydrogenation was complete (the target IV reached), a neutral bleaching clay (attapulgite-smectite clay) available from Oil-Dri Corporation of American, Chicago, Ill. under the trade designation Pure Flo B80, was added to the samples in an amount of 5% and mixed one hour at 90° C. Hydrogenation catalyst was then removed by filtration with vacuum using a Buchner funnel. The extent of hydrogenation for each sample is represented by the IV value for each Sample listed in TABLE 1. The IV for each sample was determined by AOCS Official Method Cd 1d-92. Total polyunsaturates were determined by gas chromatography (GC).

The partially hydrogenated SBO samples were subjected to ethenolysis conditions to produce methyl 9-decenoate. These key reactions demonstrate feasibility of the partial hydrogenation and metathesis reactions sequence steps.

Ethenolysis Procedure: 10.00 g of partially hydrogenated soy bean oil was loaded into a 3-oz Fisher-Porter bottle, which was then sealed with a gas regulator. The bottle was then heated to 50° C. to melt its contents and sparged with argon through the regulator inlet for 30 minutes at 50° C. The bottle was quickly opened, 9.5 mg (1,000 ppm) of C823 catalyst was added and the bottle was resealed. The reaction mixture was sparged with ethylene three times, ethylene pressure was set to 150 psi and the mixture was stirred at 50° C. After 4 hours, a 1-mL sample was removed from the bottle and transesterified by diluting with 1 mL of 1M NaOH in methanol and heating to 60° C. for 1 hour. After cooling to room temperature, 1 drop of the transesterified sample was diluted with ethyl acetate and analyzed by GC.

TABLE 2

| Ethenolysis* of Partially hydrogenated soybean oils Results of GC analysis of reaction mixture after 4 hours. | | |
|---|---|---|
| Reaction | Nature wax: | 9-Decenoate (GC %) |
| 112-123-4 hr | B-693 SBO | 6.4 |
| 112-124-4 hr | D-816 SBO | 6.0 |
| 112-125-4 hr | C-771 SBO | 7.9 |

*Ethenolysis of 10.00 g partially hydrogenated soybean oil using 9.5 mg (1000 ppm) C823 catalyst, 150 psi ethylene and 50° C. 30 minutes of degassing soybean oil with argon before catalyst addition.

Example 2

Partial Hydrogenation Procedure

Partial hydrogenation reactions were conducted using a 0.6-L Parr pressure reactor connected to a $H_2$ gas cylinder that was equipped with a two-stage valve to allow control of the $H_2$ gas pressure in the headspace of the reactor.

The partial hydrogenation reactions were run according to the following procedure:

1. 277.6 g (300 ml) of RBD soybean oil and the required amount of catalyst (Engelhard, called Cu-0202P) (see, TABLE 3) were added to the reactor.
2. The head of the reactor was attached and tightened. Next, a thermocouple wire, $H_2$ gas feed, and agitation motor were connected to the reactor head. Cooling water lines were connected to the agitator shaft. The reactor was placed in a heating mantle.
3. The $H_2$ gas cylinder valves were opened while keeping the reactor gas inlet valve closed.
4. The reactor was purged and vented three times using $N_2$ gas. After purging, $H_2$ gas was introduced to the reactor to achieve the desired $H_2$ gas pressure (see, TABLE 3). The gas inlet valve was closed.
5. The temperature was set to the desired temperature (see, TABLE 3). The agitation rate was set at 300 rpm.
6. When the reactor reached the desired temperature, the inlet $H_2$ gas valve was opened and pressure was maintained by adjusting the gas cylinder valve. The agitation rate was increased to 500 rpm.
7. The heating rate was reduced to allow the reactor to reach steady state.
8. The reaction time was started when the reactor achieved steady state.
9. Samples of ~3 mL were taken at desired intervals for compositional analysis by GC.

Gas Chromatography (GC) Procedure

Samples of partially hydrogenated soybean oil taken from the reactor were passed through a syringe filter (Acrodisic) in order to remove the catalyst and were then stored in a refrigerator. The samples were prepared for analysis by gas chromatography (GC) using the following procedure:

1. The sample was heated in a microwave oven for 1 min.
2. 2 drops of the sample (~20 mg) was transferred to a GC vial.
3. 1.5 mL of heptane was added to the vial.
4. 60 μL methyl propionate was added to the vial.
5. 100 μL 0.5 M sodium methoxide in methanol was added to the vial.
6. The vial was agitated and was allowed to react for 10 min at room temperature.
7. The sample was then analyzed via GC. The results are presented in TABLE 3.

TABLE 3

| Temperature (° C.) | Pressure (psi) | Catalyst load (wt %) | Product Composition (mole %) 18:0 | 18:1 | 18:2 | 18:3 | 16:0 |
|---|---|---|---|---|---|---|---|
| Pure Soybean Oil | | | 5% | 24% | 53% | 7% | 11% |
| 150 | 40 | 0.6 | 5% | 38% | 46% | 0% | 11% |
| 175 | 60 | 0.5 | 5% | 57% | 27% | 0% | 11% |
| 200 | 20 | 0.05 | 5% | 30% | 49% | 5% | 11% |
| 200 | 20 | 0.2 | 5% | 56% | 29% | 0% | 11% |
| 200 | 40 | 0.4 | 5% | 67% | 17% | 0% | 11% |
| 200 | 80 | 0.6 | 6% | 75% | 8% | 0% | 11%[a] |
| 200 | 80 | 0.6 | 5% | 72% | 11% | 0% | 11%[a] |
| 200 | 80 | 1.2 | 6% | 70% | 13% | 0% | 11% |
| 225 | 60 | 0.5 | 5% | 73% | 10% | 0% | 11% |
| 250 | 40 | 0.4 | 7% | 70% | 12% | 0% | 11% |

TABLE 3-continued

| Temperature | Pressure | Catalyst load | Product Composition (mole %) | | | | |
|---|---|---|---|---|---|---|---|
| (° C.) | (psi) | (wt %) | 18:0 | 18:1 | 18:2 | 18:3 | 16:0 |
| 250 | 80 | 0.6 | 10% | 70% | 8% | 0% | 11%[b] |
| 250 | 80 | 0.6 | 15% | 68% | 6% | 0% | 11%[c] |
| 200 | 80 | 0.6 | 5% | 58% | 26% | 0% | 11%[d] |

Figure 3:
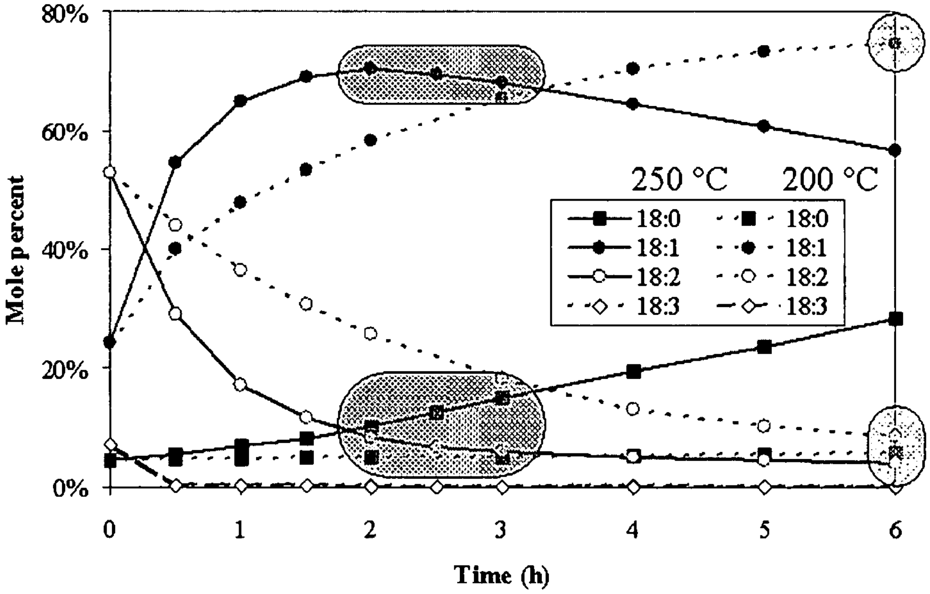
FIG. 3 is a kinetic plot of the partial hydrogenation of soybean oil at 200° C. and 250° C.

Results at t = 6 hrs and 500 rpm agitation rate, unless noted otherwise:
[a]Separate experiments;
[b]t = 2 hrs;
[c]Same trial, t = 3 hrs;
[d]Agitation rate = 200 rpm Kinetic plots for runs at 200° C. and 250° C. are presented in FIG. 3. Results are shown for both 200° C. and 250° C. at 80 psi and 0.6% Cu.

As shown in FIG. 3, after 6 hours at 200° C., the product mixture contained 74% 18:1, 10% 18:2, 6% 18:0, and a negligible amount of 18:3. For the reaction at 250° C., at 2 hours, the product mixture contained 70% 18:1, 7% 18:2, and 13% 18:0. Running the reaction for another hour resulted in a product mixture of 68% 18:1, 6% 18:2, and 15% 18:0.

Example 3

Refined, bleached, deodorized soybean oil (Cargill, Inc) was purged with argon for 1 hr to remove oxygen. The ruthenium metathesis catalyst 827 (225 ppm, on a mol/mol basis) was added to the soybean oil. The mixture was stirred at 70° C., and samples were taken during the reaction to determine the amount of benzene and 1,4-cyclohexadiene. The concentration of benzene and 1,4-cyclohexadiene were determined by GC-MS, and are shown in TABLE 4.

TABLE 4

Concentration of VOCs in metathesized soybean oil

| Materia sample | Catalyst | Catalyst (ppm mol) | Time (min) | Benzene (ppm) | 1,4-Cyclohexadiene (ppm) |
|---|---|---|---|---|---|
| 109-087 | 827 | 225 | 15 | 0 | 22,363 |
| | | | 30 | 0 | 40,087 |
| | | | 45 | 231 | 37,350 |
| | | | 60 | 350 | 37,059 |
| | | | 90 | 744 | 37,234 |
| | | | 120 | 1,098 | 41,305 |
| | | | 240 | 1,467 | 34,736 |
| | | | 480 | 1,959 | 37,181 |

Example 4

Refined, bleached, and deodorized soybean oil was partially hydrogenated using the following procedure.

Refined, bleached, deodorized soybean oil (Cargill, Inc.) and commercially available nickel catalyst (Pricat 9925, Johnson-Matthey) or copper catalyst (Cu-0202P, BASF) were charged in a 600 ml Parr pressure reactor. The Parr was purged 4 to 6 times with nitrogen at room temperature, while stirring at 300 rpm. After the last purge, the reactor was pressurized to about 20-100 psig of nitrogen. The reactor was then heated to the desired temperature (see TABLE 5). Upon reaching the desired temperature, the nitrogen was evacuated. The Parr was purged twice with about 50 psig of hydrogen gas, and the stirring was increased to 500 rpm. After the second purge, the Parr was pressured to the operating pressure (see TABLE 5), and the hydrogen line was kept open throughout the reaction. The duration of the hydrogenation reaction was dependent on operating temperature and catalyst type.

At the end of the reaction, the hydrogen gas line was disconnected, the stirring rate was decreased to 200-300 rpm, and the contents were allowed to cool to 50° C. or less. The catalyst was removed using Whatman filter paper and Celite 545 or bleaching clay as filter aid in a Buchner funnel and pulling vacuum.

Samples were analyzed by gas chromatography to determine fatty acid composition. Compositional features of the partially hydrogenated soybean oil samples 1 to 4 are summarized in TABLE 5.

TABLE 5

Fatty acid composition of partially hydrogenated soybean oil

| | Sample 1 6648-33-2E final | Sample 2 6648-33-3J final | Sample 3 6648-33-H final | Sample 4 6648-33-3H final |
|---|---|---|---|---|
| Catalyst | Pricat 9925 | Pricat 9925 | Cu-0202P | Cu-0202P |
| Catalyst Loading | 0.35 wt % | 0.35 wt % | 0.6 wt % | 0.6 wt % |
| Temperature | 150 C. | 120 C. | 200 C. | 200 C. |
| Pressure | 50 psig | 50 psig | 80 psig | 80 psig |
| Time | 120 min | 180 min | 600 min | 480 min |
| Total 18:1 | 55.17% | 71.34% | 65.72% | 66.76% |
| Total 18:2 | 0.48% | 6.02% | 4.85% | 10.92% |
| Total 18:3 | 0.02% | 0.14% | 0.10% | 0.13% |
| 14:0 (Myristic) | 0.08% | 0.07% | 0.07% | 0.07% |
| 15:0 | 0.02% | 0.02% | 0.02% | 0.02% |
| 16:0 (Palmitic) | 10.95% | 10.85% | 10.93% | 10.91% |
| 9c-16:1 (Palmitoleic) | ND | 0.07% | 0.05% | 0.07% |
| 17:0 | 0.16% | 0.11% | 0.12% | 0.12% |
| 18:0 (Stearic) | 32.21% | 10.44% | 17.26% | 10.06% |
| 4t-18:1 | 0.40% | 0.10% | ND | 0.02% |
| 5t-18:1 | 0.86% | 0.20% | 0.03% | 0.05% |
| 6t-8t-18:1 | 10.34% | 4.18% | 2.78% | 2.78% |
| 9t-18:1 | 5.20% | 4.34% | 7.23% | 5.17% |
| 10t-18:1 | 7.06% | 8.09% | 9.20% | 9.64% |
| 11t-18:1 | 5.14% | 5.73% | 7.08% | 6.85% |
| 12t-18:1 | 5.77% | 4.04% | 4.99% | 4.68% |
| 13t-14t-18:1 (6c-8c-18:1) | 8.06% | 4.48% | 3.54% | 2.71% |
| 9c-18:1 (Oleic) (14t-16t-18:1) | 2.55% | 23.41% | 17.28% | 21.46% |
| 10c-18:1 (15t-18:1) | 3.10% | 2.38% | 2.47% | 2.48% |
| 11c-18:1 (anteiso 19:0) | 1.65% | 3.07% | 2.80% | 3.10% |
| 12c-18:1 | 1.56% | 8.18% | 6.42% | 5.73% |
| 13c-18:1 | 1.13% | 0.96% | 0.78% | 0.86% |
| 16t-18:1 | 1.82% | 1.48% | 0.65% | 0.80% |
| 14c-18:1 | 0.04% | 0.09% | 0.15% | 0.11% |
| 15c-18:1 (19:0) | 0.47% | 0.62% | 0.32% | 0.32% |
| t,t-NMID_1 | 0.05% | 0.07% | 0.04% | 0.05% |
| t,t-NMID_2 | 0.02% | 0.10% | 0.15% | 0.10% |
| t,t-NMID_3 | 0.05% | 0.03% | 0.05% | 0.04% |
| t,t-NMID_4 | 0.02% | 0.01% | 0.05% | 0.03% |
| 9t,12t-18:2 | ND | 0.07% | 0.40% | 0.63% |
| 9c,13t-18:2 (8t,12c-18:2) | ND | 1.54% | 1.16% | 1.36% |
| tc/ct-18:2 | ND | ND | 0.09% | 0.07% |
| 9c,12t-18:2 | 0.35% | 0.08% | 0.89% | 2.24% |
| 8c,13c-18:2 (16t-18:1) | ND | 0.76% | 0.15% | 0.17% |
| 9t,12c-18:2 | ND | 0.33% | ND | ND |
| 9t,15c-18:2 (10t,15c-18:2) | ND | ND | 0.67% | 1.77% |
| 11t,15c-18:2 (9c,13c-18:2; 11c,14c-18:2) | ND | 0.42% | 0.24% | 0.27% |
| 9c,12c-18:2 (Linoleic) | ND | 2.25% | 0.80% | 3.97% |
| 18:2 other | ND | ND | ND | 0.04% |
| 9c,15c-18:2 | ND | 0.36% | 0.12% | 0.19% |
| 20:0 (Arachidic) | 0.42% | 0.41% | 0.40% | 0.39% |
| 11c-20:1 (Gondoic) | ND | 0.02% | 0.01% | ND |
| 9t,12c,15c-18:3 | ND | ND | ND | ND |

TABLE 5-continued

| Fatty acid composition of partially hydrogenated soybean oil | | | | |
|---|---|---|---|---|
| | Sample 1 6648-33-2E final | Sample 2 6648-33-3J final | Sample 3 6648-33-H final | Sample 4 6648-33-3H final |
| 9c,12c,15c-18:3 (Linolenic) | 0.02% | 0.14% | 0.10% | 0.13% |
| 21:0 | 0.03% | 0.02% | 0.02% | 0.03% |
| 22:0 (Behenic) | 0.33% | 0.33% | 0.34% | 0.33% |
| 23:0 | 0.03% | 0.03% | 0.03% | 0.04% |
| 24:0 (Lignoceric) | 0.10% | 0.11% | 0.10% | 0.11% |

Example 5

Samples 1-4 produced in Example 4 were then self-metathesized using the following procedure.

Partially hydrogenated soybean oil was purged with argon for 1 hr to remove oxygen. The ruthenium metathesis catalyst 827 (225 ppm, on a mol/mol basis) was added to the partially hydrogenated soybean oil. The mixture was stirred at 70° C., and samples were taken to determine the amount of benzene and 1,4-cyclohexadiene. The concentration of benzene and 1,4-cyclohexadiene were determined by GC-MS, and are shown in TABLE 6. Sample 1, which had the lowest concentration of linoleic and linolenic acid after hydrogenation, had the lowest concentration of 1,4-cyclohexadiene after metathesis.

TABLE 6

Concentration of VOCs in metathesized, partially hydrogenated oil

| Materia sample | Sample # | Catalyst | Catalyst (ppm mol) | Time (min) | Benzene (ppm) | 1,4-Cyclo-hexadiene (ppm) |
|---|---|---|---|---|---|---|
| 109-083 | Sample 3 6648-33-H final | 827 | 225 | 15 | 0 | 212 |
| | | | | 30 | 0 | 354 |
| | | | | 45 | 0 | 409 |
| | | | | 60 | 0 | 434 |
| | | | | 90 | 0 | 373 |
| | | | | 120 | 0 | 411 |
| | | | | 240 | 0 | 363 |
| | | | | 480 | 0 | 391 |
| 109-084 | Sample 4 6648-33-3H final | 827 | 225 | 15 | 0 | 727 |
| | | | | 30 | 0 | 1,545 |
| | | | | 45 | 0 | 1,545 |
| | | | | 60 | 0 | 1,646 |
| | | | | 90 | 0 | 1,566 |
| | | | | 120 | 0 | 1,373 |
| | | | | 240 | 0 | 1,460 |
| | | | | 480 | 289 | 1,525 |
| 109-085 | Sample 1 6648-33-2E final | 827 | 225 | 15 | 0 | 229 |
| | | | | 30 | 0 | 302 |
| | | | | 45 | 0 | 257 |
| | | | | 60 | 0 | 241 |
| | | | | 90 | 0 | 144 |
| | | | | 120 | 0 | 172 |
| | | | | 240 | 0 | 266 |
| | | | | 480 | 0 | 147 |
| 109-086 | Sample 2 6648-33-3J final | 827 | 225 | 15 | 0 | 589 |
| | | | | 30 | 0 | 1,257 |
| | | | | 45 | 0 | 1,542 |
| | | | | 60 | 0 | 1,394 |
| | | | | 90 | 0 | 1,429 |
| | | | | 120 | 0 | 1,346 |
| | | | | 240 | 0 | 1,477 |
| | | | | 480 | 0 | 1,490 |

Results illustrated large differences between the concentrations of 1,4-cyclohexadiene and benzene in the standard RBD soy oil (Example 3) relative to the partially hydrogenated soy oils studied (Example 5). Levels of 1,4-cyclohexadiene and benzene were lower in each of the partially hydrogenated oil metatheses samples than in the original soy oil metathesis samples. Results indicate that levels of 1,4-cyclohexadiene and benzene produced in the metathesis reaction are directly dependent upon the percent total polyunsaturates in the starting material. These results indicate that the use of partially hydrogenated soy oil can significantly reduce levels of 1,4-cyclohexadiene and benzene produced during metathesis.

Other embodiments of this invention will be apparent to those skilled in the art upon consideration of this specification or from practice of the invention disclosed herein. Variations on the embodiments described herein will become apparent to those of skill in the relevant arts upon reading this description. The inventors expect those of skill to use such variations as appropriate, and intend to the invention to be practiced otherwise than specifically described herein. Accordingly, the invention includes all modifications and equivalents of the subject matter recited in the claims as permitted by applicable law. Moreover, any combination of the above-described elements in all possible variations thereof is encompassed by the invention unless otherwise indicated. All patents, patent documents, and publications cited herein are hereby incorporated by reference as if individually incorporated. In case of conflict, the present specification, including definitions, will control.

What is claimed is:

1. A method comprising steps of:

(a) providing a polyunsaturated fatty acid composition;

(b) providing a hydrogenation catalyst;

(c) hydrogenating at least a portion of the polyunsaturated fatty acid composition in the presence of the hydrogenation catalyst to form a partially hydrogenated composition;

(d) providing a metathesis catalyst comprising a transition metal; and (e) metathesizing at least a portion of the partially hydrogenated composition in the presence of the metathesis catalyst to form a composition comprising a mixture of metathesis products, wherein the metathesizing step comprises cross-metathesizing at least a portion of the partially hydrogenated composition with a small olefin.

2. The method according to claim 1, wherein the polyunsaturated fatty acid composition comprises a polyunsaturated fatty acid, a polyunsaturated fatty monoester, a polyol ester having one or more polyunsaturated fatty acids, or a mixture thereof.

3. The method according to claim 1, wherein the polyunsaturated fatty acid composition comprises providing a natural oil.

4. The method according to claim 3, wherein the natural oil is soybean oil.

5. The method according to claim 1, wherein the step of providing a hydrogenation catalyst comprises providing a hydrogenation catalyst selected from nickel, copper, palladium, platinum, molybdenum, iron, ruthenium, osmium, rhodium, iridium, zinc, cobalt, or a combination of any of these.

6. A method comprising steps of:

(a) providing a polyunsaturated fatty acid composition;

(b) providing a hydrogenation catalyst;

(c) hydrogenating at least a portion of the polyunsaturated fatty acid composition in the presence of the hydrogenation catalyst to form a partially hydrogenated composition;

(d) providing a metathesis catalyst comprising a transition metal; and (e) metathesizing at least a portion of the partially hydrogenated composition in the presence of the metathesis catalyst to form a composition comprising a mixture of metathesis products, wherein the step of hydrogenating at least a portion of the polyunsaturated polyol ester composition comprises subjecting the polyunsaturated composition to electrocatalytic hydrogenation.

7. A method comprising steps of:

(a) providing a polyunsaturated fatty acid composition;

(b) providing a hydrogenation catalyst;

(c) hydrogenating at least a portion of the polyunsaturated fatty acid composition in the presence of the hydrogenation catalyst to form a partially hydrogenated composition;

(d) providing a metathesis catalyst comprising a transition metal; and (e) metathesizing at least a portion of the partially hydrogenated composition in the presence of the metathesis catalyst to form a composition comprising a mixture of metathesis products, wherein the partially hydrogenated composition comprises a partially hydrogenated polyol ester having an acid profile comprising monounsaturated fatty acid groups in an amount of 65 wt % or more.

8. A method comprising steps of:

(a) providing a polyunsaturated fatty acid composition;

(b) providing a hydrogenation catalyst;

(c) hydrogenating at least a portion of the polyunsaturated fatty acid composition in the presence of the hydrogenation catalyst to form a partially hydrogenated composition;

(d) providing a metathesis catalyst comprising a transition metal; and (e) metathesizing at least a portion of the partially hydrogenated composition in the presence of the metathesis catalyst to form a composition comprising a mixture of metathesis products, wherein the partially hydrogenated composition comprises a partially hydrogenated polyol ester having an acid profile comprising polyunsaturated fatty acid groups in an amount of about 10 wt % or less.

9. A method comprising steps of:

(a) providing a polyunsaturated fatty acid composition;

(b) providing a hydrogenation catalyst;

(c) hydrogenating at least a portion of the polyunsaturated fatty acid composition in the presence of the hydrogenation catalyst to form a partially hydrogenated composition;

(d) providing a metathesis catalyst comprising a transition metal; and (e) metathesizing at least a portion of the partially hydrogenated composition in the presence of the metathesis catalyst to form a composition comprising a mixture of metathesis products, wherein the partially hydrogenated composition comprises a partially hydrogenated composition having an acid profile comprising saturated fatty acid groups in an amount of 0.5 wt % to 10 wt % higher than the saturated fatty acid groups in the polyunsaturated fatty acid composition.

10. The method according to claim 7, wherein the polyunsaturated fatty acid composition is derived from soybean oil, and wherein the acid profile comprises monounsaturated fatty acid groups in an amount of 70 wt % or more.

11. The method according to claim 1, further comprising the step of removing the hydrogenation catalyst prior to the metathesizing step.

12. The method according to claim 1, wherein the step of providing a metathesis catalyst comprises providing a metal carbene catalyst selected from ruthenium, molybdenum, osmium, chromium, rhenium, tungsten, or a combination of any of these.

13. The method according to claim 1, wherein the metathesizing step comprises a self-metathesis reaction.

14. The method according to claim 13, wherein the metathesis products comprise internal olefins, monounsaturated fatty esters, and monounsaturated fatty diesters.

15. The method according to claim 14, wherein the monounsaturated fatty diesters have a chain length ranging from 8 to 32 carbon atoms.

16. The method according to claim 14, wherein at least a portion of the monounsaturated fatty esters and monounsaturated fatty diesters are in triglyceride form.

17. The method according to claim 1, wherein the small olefin is a terminal olefin selected from ethylene, propylene, 1-butene, and 1-pentene.

18. The method according to claim 1, wherein the metathesis composition comprises (i) monounsaturated fatty esters having terminal double bonds; and (ii) olefins with terminal double bonds.

19. The method according to claim 18, wherein the monounsaturated fatty esters are in triglyceride form.

20. The method according to claim 18, wherein the terminal monounsaturated fatty esters have a chain length of 4 to 16.

21. The method according to claim 18, further comprising (f) hydrolyzing at least a portion of the monounsaturated fatty esters to form monounsaturated fatty acids.

22. The method according to claim 1, wherein the hydrogenating step comprises selectively hydrogenating at least a portion of the polyunsaturated fatty acid composition in the presence of the hydrogenation catalyst, under conditions sufficient to form the partially hydrogenated composition having monounsaturated fatty acids or esters.

* * * * *

UNITED STATES PATENT AND TRADEMARK OFFICE

CERTIFICATE OF CORRECTION

PATENT NO. : 8,614,344 B2
APPLICATION NO. : 12/444791
DATED : December 24, 2013
INVENTOR(S) : Kaido et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1188 days.

Signed and Sealed this
Twenty-second Day of September, 2015

Michelle K. Lee
*Director of the United States Patent and Trademark Office*